(12) United States Patent
Kaspar et al.

(10) Patent No.: US 8,895,309 B2
(45) Date of Patent: Nov. 25, 2014

(54) MYOSTATIN INHIBITION FOR ENHANCING MUSCLE AND/OR IMPROVING MUSCLE FUNCTION

(75) Inventors: Brian K. Kaspar, Westerville, OH (US); Jerrry R. Mendell, Columbus, OH (US)

(73) Assignee: Nationwide Children's Hospital, Columbus, OH (US)

( * ) Notice: Subject to any disclaimer, the term of this patent is extended or adjusted under 35 U.S.C. 154(b) by 890 days.

(21) Appl. No.: 12/516,995

(22) PCT Filed: Nov. 29, 2007

(86) PCT No.: PCT/US2007/085960
§ 371 (c)(1),
(2), (4) Date: Mar. 22, 2010

(87) PCT Pub. No.: WO2008/067480
PCT Pub. Date: Jun. 5, 2008

(65) Prior Publication Data
US 2010/0178348 A1     Jul. 15, 2010

Related U.S. Application Data

(60) Provisional application No. 60/861,602, filed on Nov. 29, 2006.

(51) Int. Cl.
*A61P 21/00* (2006.01)
*A61K 35/76* (2006.01)
*C07K 14/015* (2006.01)

(52) U.S. Cl.
USPC ........... 435/456; 514/44; 424/93.2; 424/93.6; 435/320.1; 435/69.2

(58) Field of Classification Search
None
See application file for complete search history.

(56) References Cited

U.S. PATENT DOCUMENTS

| | | | |
|---|---|---|---|
| 5,041,538 A | 8/1991 | Ling et al. | |
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 5,942,420 A | 8/1999 | Holtzman | |
| 6,258,595 B1 | 7/2001 | Gao et al. | |
| 6,410,232 B1 | 6/2002 | Holtzman | |
| 6,537,966 B1 | 3/2003 | Duan et al. | |
| 6,566,118 B1 | 5/2003 | Atkinson et al. | |
| 6,953,662 B2 | 10/2005 | Duan et al. | |
| 7,887,793 B2 * | 2/2011 | Tremblay et al. | 424/93.21 |
| 2005/0158281 A1 * | 7/2005 | Chamberlain et al. | 424/93.2 |
| 2006/0025341 A1 * | 2/2006 | Duan et al. | 514/12 |
| 2006/0094116 A1 | 5/2006 | Colosi | |
| 2006/0251632 A1 | 11/2006 | Tremblay et al. | |
| 2007/0135336 A1 * | 6/2007 | De Kretser et al. | 514/12 |

FOREIGN PATENT DOCUMENTS

| | | |
|---|---|---|
| WO | WO-95/13365 A1 | 5/1995 |
| WO | WO-95/13392 A1 | 5/1995 |
| WO | WO-96/17947 A1 | 6/1996 |
| WO | WO 97/06243 A1 | 2/1997 |
| WO | WO-97/08298 A1 | 3/1997 |
| WO | WO-97/09441 A2 | 3/1997 |
| WO | WO-97/21825 A1 | 6/1997 |
| WO | WO-98/09657 A2 | 3/1998 |
| WO | WO-99/11764 A2 | 3/1999 |
| WO | WO-01/83692 A2 | 11/2001 |
| WO | WO-02/053703 A2 | 7/2002 |
| WO | WO-2007/053775 A1 | 5/2007 |

OTHER PUBLICATIONS

Dumonceaux et al, Combination of Myostatin Pathway Interference and Dystrophin Rescue Enhances Tetanic and Specific Force in Dystrophic mdx Mice, Molecular Therapy vol. 18 No. 5, 881-887, May 2010.*

Dumonceaux et al, Improvement of Muscle Mass Using shRNA Targeting Myostatin or Activin Receptor IIb, Molecular Therapy vol. 13, Supplement 1, May 2006, S14.*

Aalbers et al, Advancements in adeno-associated viral gene therapy approaches: exploring a new horizon, F1000 Medicine Reports 2011, 3:17, p. 1-8.*

Rizo et al., "Recombinant AAV Gene Delivery of Follistatin for Muscle Enhancement in Models of Muscular Dystrophy," Molecular Therapy 13:S352 (2006).

Snyder et al., "Efficient and stable adeno-associated virus-mediated transduction in the skeletal muscle of adult immunocompetent mice," Human Gene Therapy 8(16):1891-1900 (1997).

(Continued)

*Primary Examiner* — Maria Marvich
(74) *Attorney, Agent, or Firm* — Marshall, Gerstein & Borun LLP

(57) ABSTRACT

The present invention relates to methods for inhibiting myostatin, a regulator of muscle mass, for muscle enhancement (including inducing hypertrophy and/or hyperplasia) as well as improving muscle function (including decreasing atrophy and/or increasing endurance, force and/or strength). Some of the methods involve delivering genes to cells using viral vectors such as a recombinant Adeno-associated virus (rAAV), lentivirus or equine-associated virus, or using other delivery techniques known in the art in order to inhibit myostatin. Examples of genes to be delivered are genes encoding proteins such as Follistatin, Follistatin-related gene-1 (FLRG-1), growth differentiation factor associated protein-1 (GASP-1) and myostatin precursor propeptide. In other methods of the invention, expression of proteins such as activin IIb and myostatin is inhibited by oligonucleotide techniques to effect muscle enhancement. All the methods have applications in the treatment of musculoskeletal and neurodegenerative disorders among others, as well as enhancing muscle in livestock.

1 Claim, 21 Drawing Sheets

(56) References Cited

OTHER PUBLICATIONS

Abmayr et al., "Phenotypic Improvement of Dystrophic Muscles by rAAV/Microdystrophin Vectors Is Augmented by Igf1 Codelivery," Mol Ther., 12:441-450 (2005).

Alexander et al., "Efficacy and Safety of Edifoligide, an E2F Transcription Factor Decoy, for Prevention of Vein Graft Failure Following Coronary Artery Bypass Graft Surgery Prevent IV: A Randomized Controlled Trial," J. Am. Med. Assoc., 294:2446-2454 (2005).

Amthor et al., "Follistatin complexes Myostatin and antagonises Myostatin-mediated inhibition of myogenesis" Developmental Biol., 270:19-30 (2004).

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem., 272:11994-12000 (1997).

Bernstein et al., "Role for a bidentate ribonuclease in the initiation step of RNA interference" Nature, 409:363-366 (2001).

Bogdanovich et al., "Functional improvement of dystrophic muscle by myostatin blockade" Nature, 420:418-421 (2002).

Bogdanovich et al., "Myostatin propeptide-mediated amelioration of dystrophic pathophysiology" FASEB J, 19:543-549 (2004).

Breaker et al., "A DNA enzyme that cleaves RNA" Chem. Biol., 1:223-229 (1994).

Carter, "Adeno-associated virus vectors" Current Opinions in Biotechnology, 3:533-539 (1992).

Chao et al., "Several Log Increase in Therapeutic Transgene Delivery by Distinct Adeno-Associated Viral Serotype Vectors," Mol Ther, 2:619-623 (2000).

Chao et al., "Sustained and Complete Phenotype Correction of Hemophilia B Mice Following Intramuscular Injection of AAV1 Serotype Vectors," Mol Ther, 4:217-222 (2001).

Clark et al., "A stable cell line carrying adenovirus-inducible rep and cap genes allows for infectivity titration of adeno-associated virus vectors," Gene Therapy 3:1124-1132 (1996).

Clark et al., "Highly Purified Recombinant Adeno-Associated Virus Vectors Are Biologically Active and Free of Detectable Helper and Wild-Type Viruses," Hum. Gene Ther., 10(6):1031-1039 (1999).

Clark et al., "Recombinant Adeno-Associated Viral Vectors Mediate Long-Term Transgene Expression in Muscle," Hum Gene Ther, 8:659-669 (1997).

Crooke, "Progress in Antisense Technology: The End of the Beginning," Methods Enzymol., 313:3-45 (2000).

Cserjesi, et al., "Myogenin Induces the Myocyte-Specific Enhancer Binding Factor MEF-2 Independently of Other Muscle-Specific Gene Products," Mol Cell Biol 11:4854-4862 (1991).

Cullen, "RNA interference: antiviral defense and genetic tool," Nat. Immunol., 3:597-599 (2002).

De, et al., "High Levels of Persistent Expression of α1-Antitrypsin Mediated by the Nonhuman Primate Serotype rh.10 Adeno-associated Virus Despite Preexisting Immunity to Common Human Adeno-associated Viruses," Mol. Ther., 13(1):67-76 (2006).

Doudna et al., "Selection of an RNA molecule that mimics a major autoantigenic epitope of human insulin receptor," Proc. Natl. Acad. Sci. U.S.A., 92:2355-2359 (1995).

Duclos et al., "Progressive Muscular Dystrophy in α-Sarcoglycan-deficient Mice," J. Cell Biol., 142(6):1461-1471 (1993).

Eckstein, "Phosphorothioate Oligodeoxynucleotides: What Is Their Origin and What Is Unique About Them?," Antisense Nucleic Acid Drug Dev., 10:117-121 (2000).

Ellington, et al., "In vitro selection of RNA molecules that bind specific ligands," Nature, 346:818-822 (1990).

Fire et al., "Potent and specific genetic interference by double-stranded RNA in Caenorhabditis elegans," Nature, 391:806-811 (1998).

Francois et al., "Sequence-specific recognition of the major groove of DNA by oligodeoxynucleotides via triple helix formation. Footprinting studies," Nucleic Acids Res., 16:11431-11440 (1988).

Gao et al., "Clades of Adeno-Associated Viruses Are Widely Disseminated in Human Tissues," J. Virol., 78:6381-6388 (2004).

Gilmore et al., "The Design and Exogenous Delivery of siRNA for Post-transcriptional Gene Silencing," J. Drug Target, 12:315-340 (2004).

Gleave, et al., "Antisense Therapy for Cancer," Nat. Rev. Cancer, 5:468-479 (2005).

Gragoudas et al., "Pegaptanib for Neovascular Age-Related Macular Degeneration," N. Engl. J. Med., 351:2805-2816 (2004).

Grobet et al., "A deletion in the bovine myostatin gene causes the double-muscled phenotype in cattle," Nat Genet, 17:71-74 (1997).

Gurney et al., "Motor Neuron Degeneration in Mice That Express a Human Cu,Zn Superoxide Dismutase Mutation," Science, 264:1772-1775 (1994).

Guvakova et al., "Phosphorothioate Oligodeoxynucleotides Bind to Basic Fibroblast Growth Factor, Inhibit Its Binding to Cell Surface Receptors, and Remove it from Low Affinity Binding Sites on Extracellular Matrix," J. Biol. Chem., 270:2620-2627 (1995).

Hannon, "RNA interference," Nature, 418:244-251 (2002).

Hermonat et al., "Use of adeno-associated virus as a mammalian DNA cloning vector: Transduction of neomycin resistance into mammalian tissue culture cells," Proc. Natl. Acad. Sci. USA, 81:6466-6470 (1984).

Herzog et al., "Stable gene transfer and expression of human blood coagulation factor IX after intramuscular injection of recombinant adeno-associated virus," Proc Natl Acad Sci USA, 94:5804-5809 (1997).

Hill et al., "Regulation of Myostatin in Vivo by Growth and Differentiation Factor-Associated Serum Protein-1: A Novel Protein with Protease Inhibitor and Follistatin Domains," Mol Endocrinol, 17:1144-1154 (2003).

Hill et al., "The Myostatin Propeptide and the Follistatin-related Gene Are Inhibitory Binding Proteins of Myostatin in Normal Serum," J. Biol. Chem., 277(43):40735-40741 (2002).

Johnson et al., "Muscle Creatine Kinase Sequence Elements Regulating Skeletal and Cardiac Muscle Expression in Transgenic Mice," Mol Cell Biol, 9:3393-3399 (1989).

Kambadur et al., "Mutations in myostatin (GDF8) in Double-Muscled Belgian Blue and Piedmontese Cattle," Genome Res, 7:910-915 (1997).

Kaspar et al., "Targeted Retrograde Gene Delivery for Neuronal Protection," Mol Ther, 5:50-56 (2002).

Kessler et al., "Gene delivery to skeletal muscle results in sustained expression and systemic delivery of a therapeutic protein," Proc Nat. Acad Sc. USA, 93:14082-14087 (1996).

Khachigian, "Deoxyribozymes as Inhibitors of Vascular Smooth Muscle Cell Growth," Curr. Pharm. Biotechnol., 5:337-339 (2004).

Khachigian, "DNAzymes as molecular agents that manipulate Egr-1 gene expression," Biochem. Pharmacol., 68:1023-1025 (2004).

Kourlas, et al. "Pegaptanib Sodium for the Treatment of Neovascular Age-Related Macular Degeneration: A Review," Clin. Ther., 28:36-44 (2006).

Kruger et al., "Self-Splicing RNA: Autoexcision and Autocyclization of the Ribosomal RNA Intervening Sequence of Tetrahymena Tetrahymena," Cell, 31:147-157 (1982).

Kumar et al., "Gene targeting by ribozyme against TNF-a mRNA inhibits autoimmune arthritis," Gene Ther., 12:1486-1493 (2005).

Kurreck, "Antisense technologies Improvement through novel chemical modifications," Eur. J. Biochem., 270:1628-1644 (2003).

Laughlin et al., "Cloning of infectious adeno-associated virus genomes in bacterial plasmids," Gene, 23:65-73 (1983).

Lebkowski, et al., "Adeno-Associated Virus: a Vector System for Efficient Introduction and Integration of DNA into a Variety of Mammalian Cell Types," Mol. Cell Biology 8:3988-3996 (1988).

Lee, "Regulation of Muscle Mass by Myostatin," Ann Rev Cell Dev Biol, 20:61-86 (2004).

Lee, et al. "Regulation of myostatin activity and muscle growth," Proc Natl Acad Sci USA, 98(16):9306-9311 (2001).

Lewis et al., "Generation of Neutralizing Activity against Human Immunodeficiency Virus Type 1 in Serum by Antibody Gene Transfer," J Virol, 76:8769-8775 (2002).

(56) References Cited

OTHER PUBLICATIONS

Mader, et al., "A steroid-inducible promoter for the controlled overexpression of cloned genes in eukaryotic cells," Proc. Natl. Acad. Sci. USA 90:5603-5607 (1993).
Mann et al., "Therapeutic applications of transcription factor decoy oligonucleotides," J. Clin. Invest., 106:1071-1075 (2000).
Manoharan, "2'-Carbohydrate modifications in antisense oligonucleotide therapy: importance of conformation, configuration and conjugation," Biochim. Biophys. Acta, 1489:117-130 (1999).
Marwick, "First "Antisense" Drug Will Treat CMV Retinitis," J. Am. Med. Assoc. 280: 871 (1998).
McLaughlin et al., "Adeno-Associated Virus General Transduction Vectors: Analysis of Proviral Structures," J. Virol., 62:1963-1973 (1988).
McPherron et al., "Regulation of anterior/posterior patterning of the axial skeleton by growth/differentiation factor 11," Nat. Genet., 22:260-264 (1999).
McPherron et al., "Regulation of skeletal muscle mass in mice by a new TGF-β superfamily member," Nature, 387:83-90 (1997).
McPherron, et al., "Double muscling in cattle due to mutations in the myostatin gene," Proc Natl Acad Sci USA, 94:12457-12461 (1997).
Miller et al., "Targeting Alzheimer's disease genes with RNA interference: an efficient strategy for silencing mutant alleles," Nucleic Acids Res., 32:661-668 (2004).
Montgomery et al., "RNA as a target of double-stranded RNA-mediated genetic interference in *Caenorhabditis elegans*," Proc. Natl. Acad. Sci. U.S.A., 95:15502-15507 (1998).
Mori, et al., "Two novel adeno-associated viruses from cynomolgus monkey: pseudotyping characterization of capsid protein," Virology 330:375-383 (2004).
Morishita et al., "A gene therapy strategy using a transcription factor decoy of the E2F binding site inhibits smooth muscle proliferation in vivo," Proc. Natl. Acad. Sci. U.S.A., 92:5855-5859 (1995).
Moser, et al., "Sequence-Specific Cleavage of Double Helical DNA by Triple Helix Formation," Science, 238:645-650 (1987).
Murphy et al., "Long-term correction of obesity and diabetes in genetically obese mice by a single intramuscular injection of recombinant adeno-associated virus encoding mouse leptin," Proc Natl Acad Sci USA, 94:13921-13926 (1997).
Muscat et al., "Multiple 5'-Flanking Regions of the Human α-Skeletal Actin Gene Synergistically Modulate Muscle-Specific Expression," Mol Cell Biol, 7:4089-4099 (1987).
Muzyczka, "Use of Adeno-Associated Virus as a General Transduction Vector for Mammalian Cells," Current Topics in Microbiology and Immunology, 158:97-129 (1992).
Nimjee et al., "Aptamers: An Emerging Class of Therapeutics," Annu. Rev. Med., 56:555-583 (2005).
Nimjee et al., "A Novel Antidote-Controlled Anticoagulant Reduces Thrombin Generation and Inflammation and Improves Cardiac Function in Cardiopulmonary Bypass Surgery," Mol. Ther., 14:408-415 (2006).
Nykanen et al., "ATP Requirements and Small Interfering RNA Structure in the RNA Interference Pathway," Cell, 107:309-321 (2001).
Patil, "DNA-based Therapeutics and DNA Delivery Systems: A Comprehensive Review," AAPS J. 7:E61-E77 (2005).
Paul et al. "Increased Viral Titer Through Concentration of Viral Harvests from Retroviral Packaging Lines," Human Gene Therapy 4:609-615 (1993).
Perrin et al., "An experimental rabies vaccine produced with a new BHK-21 suspension cell culture process: use of serum-free medium and perfusion-reactor system," Vaccine 13:1244-1250 (1995).
Rabinowitz et al., "Cross-Packaging of a Single Adeno-Associated Virus (AAV) Type 2 Vector Genome into Multiple AAV Serotypes Enables Transduction with Broad Specificity," J. Virol., 76:791-801 (2002).

Ralph et al., "Silencing mutant SOD1 using RNAi protects against neurodegeneration and extends survival in an ALS model," Nat. Med., 11:429-433 (2005).
Reynolds et al., "Rational siRNA design for RNA interference," Nat. Biotechnol., 22:326-330 (2004).
Ruffing et al., "Mutations in the earboxy terminus of adeno-associated virus 2 capsid proteins affect viral infectivity: lack of an RGD integrin-binding motif ," J Gen Virol, 75:3385-3392 (1994).
Rusconi et al., "RNA aptamers as reversible antagonists of coagulation factor IXa," Nature, 419:90-94 (2002).
Samulski, et al., "Helper-Free Stocks of Recombinant Adeno-Associated Viruses: Normal Integration Does Not Require Viral Gene Expression," J. Virol., 63:3822-3828 (1989).
Samulski et al., "Cloning of adeno-associated virus into pBR322: Rescue of intact virus from the recombinant plasmid in human cells," Proc. Natl. Acad. S6. USA, 79:2077-2081 (1982).
Tratschin et al., "A Human Parvovirus, Adeno-Associated Virus, as a Eucaryotic Vector: Transient Expression and Encapsidation of the Procaryotic Gene for Chloramphenicol Acethltransferase," Mol. Cell. Biol. 4:2072-2081 (1984).
Tratschin et al., "Adeno-Associated Virus Vector for High-Frequency Integration, Expression, and Rescue of Genes in Mammalian Cells," Mol. Cell. Biol. 5:3251-3260 (1985).
Trulzsch, et al., "Applications of nucleic acid technology in the CNS," J. Neurochem., 88:257-265 (2004).
Tuerk, et al., "Systematic Evolution of Ligands by Exponential Enrichment: RNA Ligands to Bacteriophage T4 DNA Polymerase," Science, 249:505-510 (1990).
Schenpp, et al., "Highly Purified Recombinant Adeno-Associated Virus Vectors," Methods Mol. Med., 69:427-443 (2002).
Schuelke et al., "Myostatin Mutation Associated with Gross Muscle Hypertrophy in a Child," N Eng J Med, 350:2682-2688 (2004).
Semenza et al., "Hypoxia-inducible nuclear factors bind to an enhancer element located 3' to the human erythropoietin gene," Proc Natl Acad Sci USA, 88:5680-5684 (1991).
Senapathy, et al., "Molecular Cloning of Adeno-associated Virus Variant Genomes and Generation of Infectious Virus by Recombination in Mammalian Cells," J. Biol. Chem., 259:4661-4666 (1984).
Sierakowska et al., "Repair of thalassemic human β-globin mRNA in mammalian cells by antisense oligonucleotides," Proc. Natl. Acad. Sci. USA, 93:12840-12844 (1996).
Sigurdsson, et al., "Structure-function relationships of hammerhead ribozymes: from understanding to applications," Trends Biotechnol., 13:286-289 (1995).
Soutschek et al., "Therapeutic silencing of an endogenous gene by systemic administration of modified siRNAs," Nature, 432:173-178 (2004).
Srivastava et al., "Nucleotide Sequence and Organization of the Adeno-Associated Virus 2 Genome," J. Virol., 45:555-564 (1983).
Tobin, et al., "Myostatin, a negative regulator of muscle mass: implications for muscle degenerative diseases," Curr Opin Pharma, 5:328-332 (2005).
Tomita, et al., "Antisense Oligonucleotides as a Powerful Molecular Strategy for Gene Therapy in Cardiovascular Diseases," Curr. Pharm. Des., 10:797-803 (2004).
Uhlenbeck, "A small catalytic oligoribonucleotide," Nature, 328:596-600 (1987).
Vinores, "Technology evaluation: Pegaptanib, Eyetech/Pfizer," Curr. Opin. Mol. Ther., 5:673-679 (2003).
Wagner et al., "Loss of Myostatin Attenuates Severity of Muscular Dystrophy in *mdx* Mice," Ann Neurol, 52:832-836 (2002).
Wagner, "Muscle regeneration through myostatin inhibition," Curr Opin Rheumatol, 17:720-724 (2005).
Weintraub et al., "The *myoD* Gene Family: Nodal Point During Specification of the Muscle Cell Lineage ," Science, 251:761-766 (1991).
White et al., "Generation of Species Cross-reactive Aptamers Using "Toggle" SELEX," Mol. Ther., 4:567-573 (2001).
Whittemore et al., "Inhibition of myostatin in adult mice increases skeletal muscle mass and strength," Biochem Biophys Res Commun, 300:965-971 (2003).

(56) References Cited

OTHER PUBLICATIONS

Wolfman et al., "Activation of latent myostatin by the BMP-1/tolloid family of metalloproteinases," Proc Natl Acad Sci US, 100:15842-15846 (2003).

Xia et al., "RNAi suppresses polyglutamine-induced neurodegeneration in a model of spinocerebellar ataxia," Nat. Med., 10:816-820 (2004).

Xiao, et al., "Production of High-Titer Recombinant Adeno-Associated Virus Vectors in the Absence of Helper Adenovirus," J. Virol., 72(3):2224-2232 (1998).

Xiao et al., "Efficient Long-Term Gene Transfer into Muscle Tissue of Immunocompetent Mice by Adeno-Associated Virus Vector," J Virol, 70:8098-8108 (1996).

Zimmers et al., "Induction of Cachexia in Mice by Systemically Administered Myostatin," Science, 296(5572):1486-1488 (2002).

Patel, "Molecules in Focus Follistatin", The International Journal of Biochemistry & Cell Biology, 30:1087-1093 (1998).

Rolling, "Recombinant AAV-mediated gene transfer to the retina: gene therapy perspectives," Gene Therapy, 11:S26-S32 (2004).

Zolotukhin, "Production of Recombinant Adeno-Associated Virus Vectors," Human Gene Therapy 16:551-557 (2005).

* cited by examiner

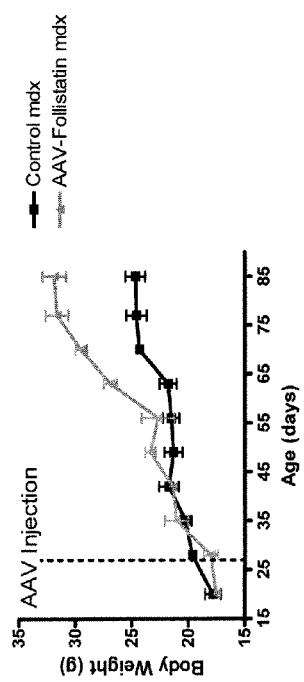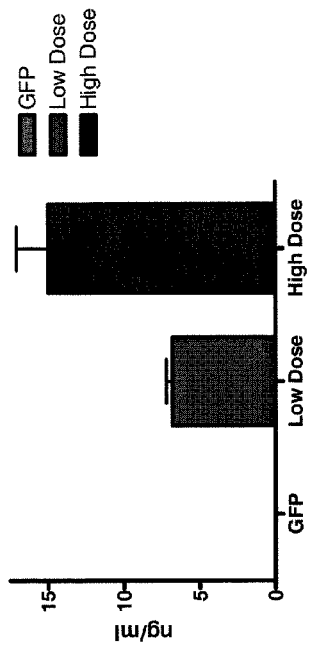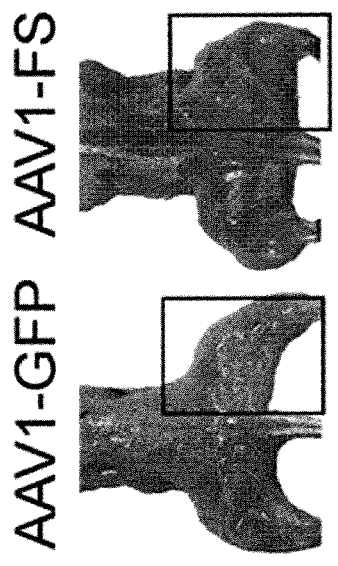
Figure 1

Diaphragms from Mdx Animals Stained with Masson's Trichrome
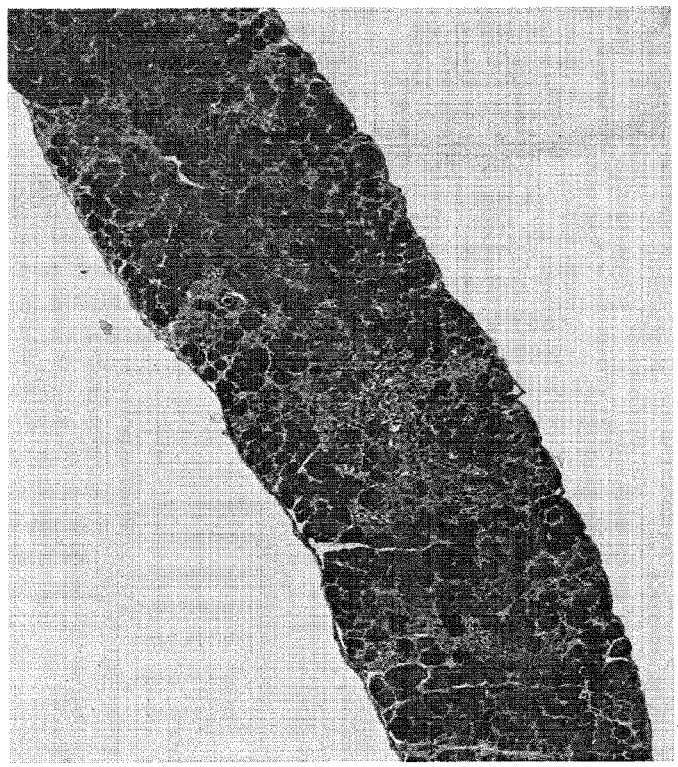
GFP-treated (10X)
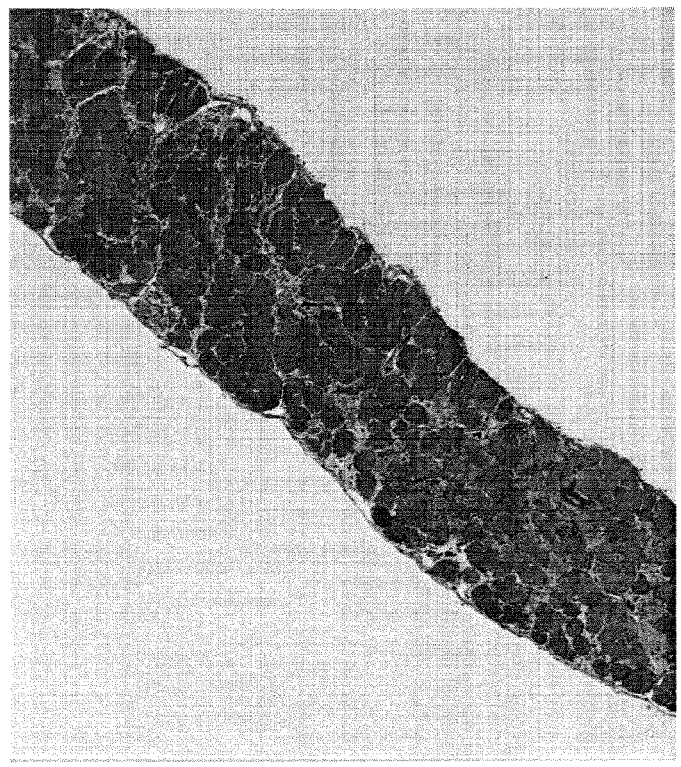
Follistatin-treated (10X)
Figure 12

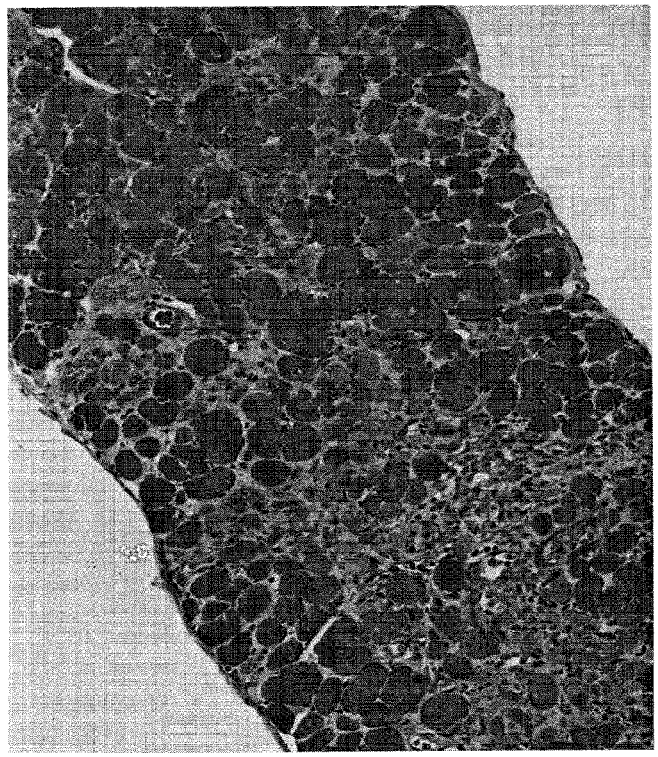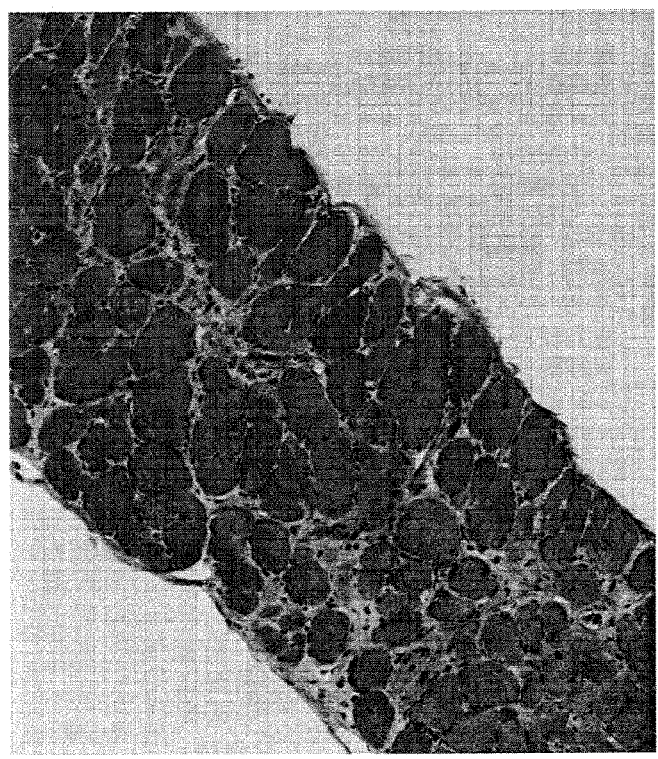
Diaphragms from Mdx Animals Stained with Masson's Trichrome
GFP-treated (20X)
Follistatin-treated (20X)
Figure 13

Diaphragms from Mdx Animals Stained with Masson's Trichrome
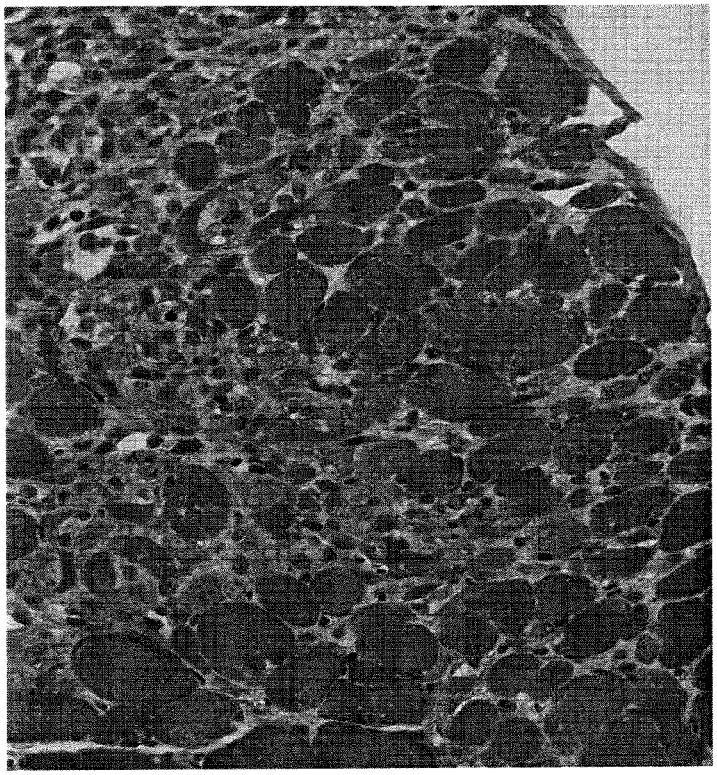
GFP-treated (40X)
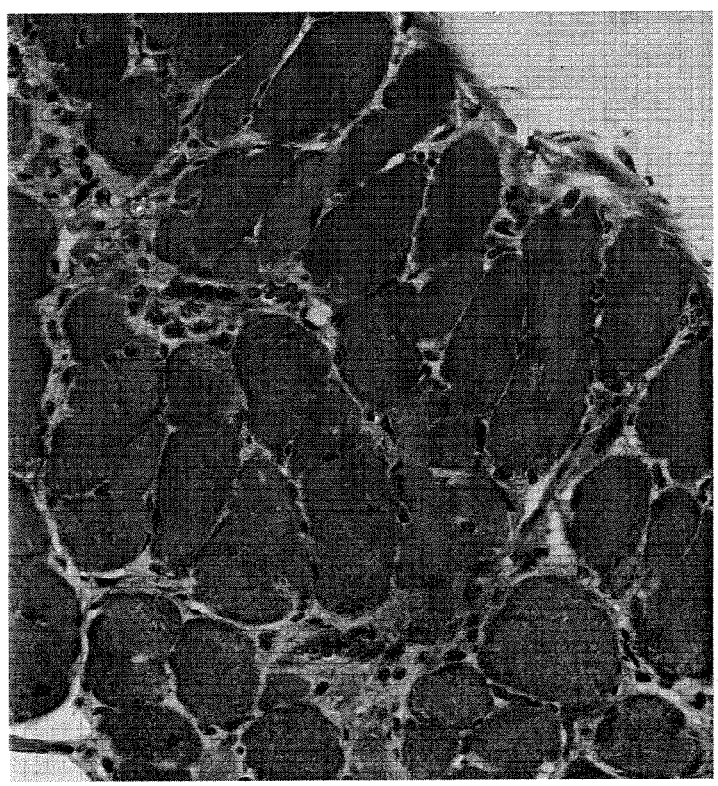
Follistatin-treated (40X)
Figure 14

Follistatin Treated Animals Demonstrate Higher Numbers of Revertant Fibers
In Gastrocnemius
Control C57/B10
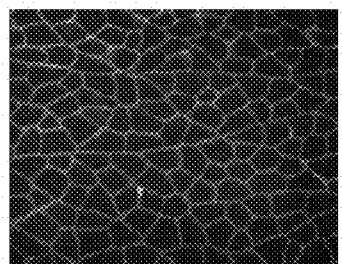
AAV-GFP
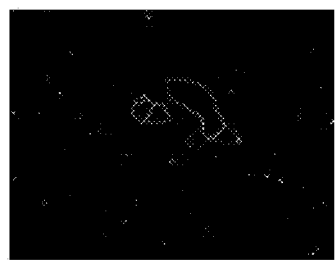
9 revertant fibers per section
AAV-Follistatin
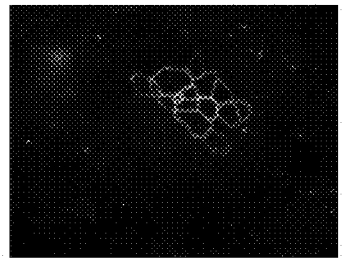
46 revertant fibers per section
Figure 16

Hindlimb grip strength is significantly increased (p<0.05) at 275 days and beyond in aged *mdx* mice treated with AAV1-FS at 210 days of age (n=10). FS = high dose AAV1-FS, GFP = AAV1-GFP controls. Error bars represent standard error.

MYOSTATIN INHIBITION FOR ENHANCING MUSCLE AND/OR IMPROVING MUSCLE FUNCTION

This invention was developed with partial government support under grant number NS052530 from the National Institutes of Health and Project A.L.S. The government may have certain rights in the invention.

FIELD OF THE INVENTION

The present invention relates to methods for inhibiting myostatin, a regulator of muscle mass, for enhancing muscle (including inducing hypertrophy and/or hyperplasia) as well as improving muscle function (including decreasing atrophy and/or increasing endurance, force and/or strength). Some of the methods involve delivering genes to cells using gene delivery or other delivery techniques known in the art in order to inhibit myostatin. Examples of genes to be delivered are genes encoding proteins such as Follistatin, Follistatin-related gene-1 (FLRG-1), growth differentiation factor associated protein-1 (GASP-1) and myostatin precursor propeptide. The genes can be delivered using, for example, a recombinant Adeno-associated virus (rAAV), lentivirus or equine-associated virus capable of infecting the cells. Following introduction, the genes are expressed in the cell body of the infected cell and the encoded proteins are secreted systemically. In other methods of the invention, expression of proteins such as activin IIb and myostatin is inhibited by oligonucleotide techniques to effect muscle enhancement and/or improve muscle function. All the methods have applications in the treatment of musculoskeletal and neurodegenerative disorders among others, as well as enhancing muscle in livestock.

BACKGROUND

Molecular advances have provided greater understanding of skeletal muscle diseases, such as muscular dystrophy (MD), beginning with the discovery of the dystrophin gene and its gene product. There are nine types of MD, each a genetic degenerative disease primarily affecting voluntary muscles. Duchenne muscular dystrophy (DMD) affects 1 in 3500 live male births. The progressive muscle weakness and degeneration usually lead to loss of ambulation and wheelchair dependency in the early teens. Death occurs anytime after age 18 due to respiratory infection usually complicated by cardiac failure. The disease is caused by mutations in the dystrophin gene, which encodes a large (427 kDa) cytoskeletal protein in both skeletal and cardiac muscle. The dystrophin gene is the largest gene identified to date. It shows one of the highest sporadic mutation rates, with 1 of every 10,000 germ cells showing de novo mutations. Thus, the high incidence (1/3500), de novo mutations, early morbidity and fatality, and the lack of effective treatment require urgency in the search for novel therapeutics. Since DMD was described more than 140 years ago, the life-span of the DMD patient has only been marginally prolonged and the quality of life may not have changed significantly improved despite tremendous advances in medicine. Few treatments have been added to the current repertoire. In the muscular dystrophies, only corticosteroids have altered the natural history of disease and indeed the mechanism of action of corticosteroids in DMD remains unknown. In fact, the known myopathic effects of steroids might predict a deleterious effect but instead there is a paradoxical response resulting in an increase in muscle mass contrasting with the effects in normal muscle. Unfortunately the benefit of steroids comes at a high cost in terms of side effects (bone loss, cataracts, delayed puberty, weight gain and hypertension) providing compelling reasons to find other approaches.

Amyotrophic Lateral Sclerosis (ALS) is another disease that results in loss of muscle and/or muscle function. First characterized by Charcot in 1869, it is a prevalent, adult-onset neurodegenerative disease affecting nearly 5 out of 100,000 individuals. ALS occurs when specific nerve cells in the brain and spinal cord that control voluntary movement gradually degenerate. Within two to five years after clinical onset, the loss of these motor neurons leads to progressive atrophy of skeletal muscles, which results in loss of muscular function resulting in paralysis, speech deficits, and death due to respiratory failure. The genetic defects that cause or predispose ALS onset are unknown, although missense mutations in the SOD-1 gene occurs in approximately 10% of familial ALS cases, of which up to 20% have mutations in the gene encoding Cu/Zn superoxide dismutase (SOD1), located on chromosome 21. SOD-1 normally functions in the regulation of oxidative stress by conversion of free radical superoxide anions to hydrogen peroxide and molecular oxygen. To date, over 90 mutations have been identified spanning all exons of the SOD-1 gene. Some of these mutations have been used to generate lines of transgenic mice expressing mutant human SOD-1 to model the progressive motor neuron disease and pathogenesis of ALS.

Another musculoskeletal disorder, inclusion body myositis (IBM), was originally named by Yunis and Samaha in 1971 to describe a patient with a chronic inflammatory myopathy who had intranuclear and intracytoplasmic tubular filaments within muscle fibers on electron microscopy. Many clinical and pathologic studies over more than three decades have supported this condition as a disorder distinct from other idiopathic inflammatory myopathies. Although incidence and prevalence statistics need further refinement, it is unequivocally the most common acquired muscle disease occurring after age of 50, with an estimated prevalence at 4-9:1,000, 000. More men are affected than women by a ratio of greater than 2:1. Typically IBM is a sporadic disorder with insidious onset, and distinctive clinical and histopathological features (sIBM). Inflammation is prominent, helping to distinguish it from the group of inherited disorders (hIBM). These include autosomal recessive and dominant conditions with pathologic features resembling sIBM without inflammatory infiltration. Perhaps the best characterized hIBM is associated with mutations of UDP-N-acetylglucosamine 2-epimerase/N-acetylmannosamine kinase (GNE) [6].

The clinical features of sIBM include an average time of about 6 years from symptom onset to diagnosis. Difficulty with ambulation and frequent falls can be attributed to weak knee extensor muscles. Early involvement of the quadriceps and forearm flexor muscle compartment is typical. This is accompanied by a scooped-out appearance of the medial aspect of the forearms and thin, atrophic quadriceps muscles. Quadriceps atrophy and weakness is directly related to loss of safe ambulation. Frequent, sudden falls occur in three-fourths of cases and are the prime reason for wheelchair use. Only a minority are totally wheelchair dependent (~15%). Mean time between symptom onset and wheelchair use ranged from 13±8 (6-32) years. Clinical dysphagia is common with estimates reaching as high as 66%. Finger flexor weakness can be detected early in the course of illness. About 40% of patients have facial muscle weakness. In the only prospective study of decline of muscle strength, the investigators documented a 4% decline in 6 months (0.66% per month) based on quantitative myometry using maximal isometric contraction testing. A similar rate of decline was also found in another study using manual muscle testing. Natural history studies document a fairly consistent, slow rate of decline in most patients with sIBM.

Therapy for sIBM has focused on the underlying inflammatory response with either immunosuppressive or immunomodulating drugs. Uncontrolled trials with corticosteroids, cyclophosphamide, chlorambucil, azathioprine and cyclosporin, and methotrexate fail to show convincing evidence of benefit. An initial pilot study of IVIG in IBM showed encouraging results but a subsequent randomized controlled trial with IVIG was negative. A prospective, double-blind, placebo-controlled, 6 month trial of weekly IM injections of 30 μg of β-interferon-1a showed no benefit. A recently published open-label trial using etanercept showed increased hand grip strength without any other functional benefits. Considering the complexity of pathogenic factors, it may be sometime before an effective treatment can target both autoimmune and myodegenerative factors. Attention has shifted to growth modulatory approaches. In a 3 month, randomized, placebo-controlled, crossover study of oxandrolone, a synthetic anabolic steroid, a borderline significant improvement in overall strength was reported, as measured by quantitative myometry. The study was limited by small sample size and short duration of treatment. Exercise is another means of growth modulation and this has been tried in inflammatory muscle diseases. An increase in isometric torque and an improvement in functional activities was reported in five patients with sIBM following a 12-week isotonic training program for the knee extensors and flexors and the elbow and wrist flexors. The small sample size disallows any conclusion but exercise had no deleterious effects based on muscle biopsies performed pre- and post-exercise.

Research has shown that skeletal muscle utilizes a regulatory mechanism to control tissue mass. In a screen for novel members of the transforming growth factor-β (TGF-β) superfamily of growth and differentiation factors, myostatin [previously called growth and differentiation factor-8 (GDF-8)] was identified and has subsequently been shown to be a negative regulator of muscle formation. Myostatin is expressed in the myotome compartment of developing somites at E9.5 with expression continuing throughout adulthood, predominantly in skeletal muscles and adipose tissue. Myostatin is synthesized in a precursor form that undergoes two proteolytic processing events to remove the N-terminal signal sequence and the C-terminal fragment, which possess receptor-binding activity. Following proteolytic processing, the propeptide and the disulfide linked C-terminal dimer remain bound noncovalently in a latent complex. Myostatin can be activated by dissociation of the propeptide after proteolytic cleavage by a metalloproteinase of the bone morphogenic (BMP)/tolloid family. The dissociated C-terminal fragment is thus the biologically active species. For a review of the biosynthesis and signaling pathway of myostatin, see Lee, *Ann Rev Cell Dev Biol*, 20: 61-86 (2004).

Myostatin is conserved among species, especially in its C-terminal fragment which is identical across human, rat, murine, porcine, turkey and chicken species. Mutations within myostatin have been shown to be linked to the double muscling phenotype in cattle [Grobet et al., *Nat Genet*, 17: 71-74 (1997); Kambadur et al., *Genome Res*, 7:910-915 (1997); and McPherron and Lee, *Proc Natl Acad Sci USA*, 94:12457-12461 (1997)] and gross muscle hypertrophy in human subjects [Schuelke et al., *N Eng J Med*, 350: 2682-2688 (2004)]. Forced muscle atrophy has even been achieved with recombinant myostatin administration or over-expression of myostatin [Zimmers et al., *Science*, 296(5572): 1486-1488 (2002)]. Histology of muscles from myostatin null mice shows increased muscle mass resulting from hyperplasia and hypertrophy of the muscle with less fat and connective tissues. The hypothesis that it may be beneficial to block, remove, or reduce myostatin to promote regeneration and reduce fibrosis in MD has been explored in animal studies. Wagner et al., *Ann Neurol*, 52: 832-836 (2002) describes data obtained from crossing myostatin null mutant mice with mdx mice (which are models for dystrophin deficiency) showing that mdx mice lacking myostatin were stronger and more muscular than their mdx counterparts. In addition, Bogdanovich et al., *Nature*, 420: 418-421 (2002) report that when a neutralizing antibody to myostatin was administered to 4 week old mdx mice by intraperitoneal injection, an increase in body weight, muscle mass, muscle size and absolute muscle strength along with a significant decrease in muscle degeneration and concentrations of serum creatine kinase was observed. Similarly, Whittemore et al., *Biochem Biophys Res Commun*, 300: 965-971 (2003) describes that myostatin neutralizing antibodies increase muscle mass in adult mice. Tobin and Celeste, *Curr Opin Pharma*, 5: 328-332 (2005) reviews the myostatin pathway as well as studies testing the effects of reducing myostatin expression/activity.

Another review article, Wagner, *Curr Opin Rheumatol*, 17: 720-724 (2005), lists various therapeutic approaches of inhibiting myostatin that have been considered for treating human disease. For example, Wyeth has developed a humanized, anti-myostatin antibody called MYO-029 for clinical trials for treatment of muscular dystrophy in adult patients. The review article states the antibody or similar agent will hopefully be tested in other indications such as inflammatory myopathies, cachexia and sarcopenia. The author also notes that a number of endogenous inhibitors of myostatin, including the myostatin propeptide, follistatin, FLRG and GASP-1 could be modified for use as therapeutic agents. The review refers to two articles describing the effects of modified propeptide on muscle in mice, Wolfman et al., *Proc Natl Acad Sci US*, 100: 15842-15846 (2003) and Bogdanovich et al., *FASEB J*, 19: 543-549 (2004).

The Wagner review article states that there is significant data that follistatin is an in vivo inhibitor of myostatin and refers to the results of studies described in Lee and McPherron, *Proc Natl Acad Sci USA*, 98(16): 9306-9311 (2001) and Amthor et al., *Developmental Biol.*, 270: 19-30 (2004) to support that statement. Follistatin is a secreted protein that inhibits the activity of TGF-β family members such as GDF-11/BMP-11. Follistatin-344 is a follistatin precursor that undergoes peptide cleavage to form the circulating Follistatin-315 isoform which includes a C-terminal acidic region. It circulates with myostatin propeptide in a complex that includes two other proteins, follistatin related gene (FLRG) and GDF associated serum protein (GASP-1). Follistatin-317 is another follistatin precursor that undergoes peptide cleavage to form the membrane-bound Follistatin-288 isoform. The DNA and amino acid sequences of the follistatin-344 precursor are respectively set out in SEQ ID NOs: 3 and 4. The Follistatin-288 isoform, which lacks a C-terminal acidic region, exhibits strong affinity for heparin-sulfate-proteoglycans, is a potent suppressor of pituitary follicle stimulating hormone, is found in the follicular fluid of the ovary, and demonstrates high affinity for the granulose cells of the ovary. The testis also produce Follistatin-288. The DNA and amino acid sequences of the follistatin-317 precursor are respectively set out in SEQ ID NOs: 5 and 6. Lack of follistatin results in reduced muscle mass at birth.

In the experiments described in the Lee and McPherron article, follistatin was over-expressed in transgenic mice. The mice showed increased muscling resulting from a combination of hyperplasia (increased muscle fiber number) and hypertrophy (increased muscle fiber diameter). The article proposes that follistatin binds the C-terminal dimer of myostatin and, in turn, inhibits the ability of myostatin to bind to activin type II receptors. Transgenic mice expressing high levels of myostatin propepetide or a dominant-negative form of activin type II receptor (Act RIIB) were also shown to exhibit increased muscle mass in the article.

The Amthor et al. article is stated to report that follistatin directly binds myostatin with high affinity, is co-expressed with myostatin in somites and prevents myostatin-mediated inhibition of limb muscle development in chick embryos. Indicating that the inhibitory effects of follistatin are not specific to myostatin evening in regard to muscle growth, the Wagner review article alternatively indicates that FLRG and GASP-1, which bind to and inhibit circulating myostatin, may prove to be specific inhibitors of myostatin for therapeutic use. FLRG is a protein that exhibits homology to a 10-cysteine repeat in follistatin. Hill et al., *J Biol Chem,* 277(43): 40735-40741 reports that FLRG binds circulating myostatin in vivo.

Yet another review article addressing the regulation of muscle mass by myostatin and clinical implications is Lee, *Annu Rev Cell Dev Biol.,* 20: 61-86 (2404).

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol,* 45: 555-564 (1983) as corrected by Ruffing et al., *J Gen Virol,* 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther,* 8: 659-669 (1997); Kessler et al., *Proc Nat. Acad Sc. USA,* 93: 14082-14087 (1996); and Xiao et al., *J Virol,* 70: 8098-8108 (1996). See also, Chao et al., *Mol Ther,* 2:619-623 (2000) and Chao et al., *Mol Ther,* 4:217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA,* 94: 5804-5809 (1997) and Murphy et al., *Proc Natl Acad Sci USA,* 94: 13921-13926 (1997). Moreover, Lewis et al., *J Virol,* 76: 8769-8775 (2002) demonstrated that skeletal myofibers possess the necessary cellular factors for correct antibody glycosylation, folding, and secretion, indicating that muscle is capable of stable expression of secreted protein therapeutics.

BRIEF SUMMARY OF THE INVENTION

The present invention provides methods and materials useful for muscle enhancement and/or improving muscle function. The methods of the invention involve delivering inhibitors of myostatin, a regulator of muscle mass, to muscle cells. Use of the methods and materials is indicated, for example, for treating musculoskeletal diseases/disorders and neurodegenerative diseases/disorders in which muscle is adversely affected as well as treating sarcopenia, cachexia, obesity, Type II diabetes, Pompe disease and lysosomal storage disorders. The methods and materials are also useful, for example, for muscle enhancement in livestock including, but not limited to, cattle, pigs and fowl.

The terms "inhibitor of myostatin" and "myostatin inhibitor" are intended to be interchangeable herein. The myostatin inhibitor may be a protein or may be an oligonucleotide (RNA or DNA). The terms "muscle enhancement" and "enhancing muscle" are also intended to be interchangeable herein and include, but are not limited to, inducement of hyperplasia (increased muscle fiber number), inducement of hypertrophy (increased muscle fiber diameter) or both. "Enhanced muscle performance" includes, but is not limited to, one or more of decreased atrophy, increased muscle endurance, increased muscle force and increased muscle strength.

Myostatin inhibitor proteins according to the invention may be peptides or polypeptides. The proteins may inhibit myostatin by binding myostatin [McPherron et al., *Nature,* 387(6628): 83-90 (1997)] or by binding the myostatin receptor activin IIb [McPherron et al., *Nat. Genet.,* 22(3): 260-264 (1999)]. Examples of proteins that inhibit myostatin by binding to myostatin are myostatin propeptide, follistatin [Shimasaki et al., U.S. Pat. No. 5,041,538], other follistatin-like proteins (U.S. Pat. Nos. 5,942,420; 6,410,232; 6,537,966; and 6,953,662), FLRG (SEQ ID NO: 8, the corresponding nucleotide sequence is SEQ ID NO: 7) [Hill et al., *J. Biol. Chem.,* 277(43): 40735-40741 (2002)] and GASP-1 (SEQ ID NO: 10, corresponding nucleotide sequence is SEQ ID NO: 9) [Hill et al., *Mol Endocrinol,* 17: 1144-1154 (2003)]. Proteins that are myostatin inhibitors according to the invention may be protein fragments or may be chimeric (i.e., fusion) proteins.

Myostatin inhibitor oligonucleotides of the invention may be antisense oligonucleotides [Eckstein, *Antisense Nucleic Acid Drug Dev.*, 10: 117-121 (2000); Crooke, *Methods Enzymol.*, 313: 3-45 (2000); Guvakova et al., *J. Biol. Chem.*, 270: 2620-2627 (1995); Manoharan, *Biochim. Biophys. Acta*, 1489: 117-130 (1999); Baker et al., *J. Biol. Chem.*, 272: 11994-12000 (1997); Kurreck, *Eur. J. Biochem.*, 270: 1628-1644 (2003); Sierakowska et al., *Proc. Natl. Acad. Sci. USA*, 93: 12840-12844 (1996); Marwick, *J. Am. Med. Assoc.* 280: 871 (1998); Tomita and Morishita, *Curr. Pharm. Des.*, 10: 797-803 (2004); Gleave and Monia, *Nat. Rev. Cancer*, 5: 468-479 (2005) and Patil, *AAPS J.* 7: E61-E77 (2005], triplex oligonucleotides [Francois et al., *Nucleic Acids Res.*, 16: 11431-11440 (1988) and Moser and Dervan, *Science*, 238: 645-650 (1987)], ribozymes/deoxyribozymes (DNAzymes) [Kruger et al., *Tetrahymena. Cell*, 31: 147-157 (1982); Uhlenbeck, *Nature*, 328: 596-600 (1987); Sigurdsson and Eckstein, *Trends Biotechnol.*, 13 286-289 (1995); Kumar et al., *Gene Ther.*, 12: 1486-1493 (2005); Breaker and Joyce, *Chem. Biol.*, 1: 223-229 (1994); Khachigian, *Curr. Pharm. Biotechnol.*, 5: 337-339 (2004); Khachigian, *Biochem. Pharmacol.*, 68: 1023-1025 (2004) and Trulzsch and Wood, *J. Neurochem.*, 88: 257-265 (2004)], small-interfering RNAs/RNAi [Fire et al., *Nature*, 391: 806-811 (1998); Montgomery et al., *Proc. Natl. Acad. Sci. U.S.A.*, 95: 15502-15507 (1998); Cullen, *Nat. Immunol.*, 3: 597-599 (2002); Hannon, *Nature*, 418: 244-251 (2002); Bernstein et al., *Nature*, 409: 363-366 (2001); Nykanen et al., *Cell*, 107: 309-321 (2001); Gilmore et al., *J Drug Target.*, 12: 315-340 (2004); Reynolds et al., *Nat. Biotechnol.*, 22: 326-330 (2004); Soutschek et al., *Nature*, 432173-178 (2004); Ralph et al., *Nat. Med.*, 11: 429-433 (2005); Xia et al., *Nat. Med.*, 10816-820 (2004) and Miller et al., *Nucleic Acids Res.*, 32: 661-668 (2004)], aptamers [Ellington and Szostak, *Nature*, 346: 818-822 (1990); Doudna et al., *Proc. Natl. Acad. Sci. U.S.A.*, 92: 2355-2359 (1995); Tuerk and Gold, *Science*, 249: 505-510 (1990); White et al., *Mol. Ther.*, 4: 567-573 (2001); Rusconi et al., *Nature*, 419: 90-94 (2002); Nimjee et al., *Mol. Ther.*, 14: 408-415 (2006); Gragoudas et al., *N Engl. J. Med.*, 351: 3805-2816 (2004); Vinores, *Curr. Opin. Mol. Ther.*, 5673-679 (2003) and Kourlas and Schiller et al., *Clin. Ther.*, 28 36-44 (2006)] or decoy oligonucleotides [Morishita et al., *Proc. Natl. Acad. Sci. U.S.A.*, 92: 5855-5859 (1995); Alexander et al., *J. Am. Med. Assoc.*, 294: 2446-2454 (2005); Mann and Dzau, *J. Clin. Invest.*, 106: 1071-1075 (2000) and Nimjee et al., *Annu. Rev. Med.*, 56: 555-583 (2005). The myostatin inhibitor oligonucleotides inhibit the expression of myostatin or expression of its receptor activin IIb. The foregoing documents are hereby incorporated by reference in their entirety herein, with particular emphasis on those sections of the documents relating to methods of designing, making and using oligonucleotides.

Some embodiments of the invention exploit the unique properties of AAV to deliver polynucleotides encoding myostatin inhibitors to muscle cells. Other embodiments of the invention utilize other vectors (for example, other viral vectors such as adenovirus, retrovirus, lentivirus, equine-associated virus, alphavirus, pox viruses, herpes virus, polio virus, sindbis virus and vaccinia viruses) to deliver polynucleotides encoding myostatin inhibitors.

DETAILED DESCRIPTION OF THE INVENTION

In one aspect, the invention provides rAAV genomes. The rAAV genomes comprise one or more AAV ITRs flanking a polynucleotide encoding one or more myostatin inhibitors. If the polynucleotide encodes one or more myostatin inhibitor proteins the polynucleotide is operatively linked to transcriptional control DNA, specifically promoter DNA and polyadenylation signal sequence DNA that are functional in target cells to form a gene cassette. The gene cassette may also include intron sequences to facilitate processing of the RNA transcript when expressed in mammalian cells. Alternatively, the polynucleotide in the rAAV genome be a myostatin inhibitor RNA or may encode one or more myostatin inhibitor RNAs. The myostatin inhibitor RNAs may be antisense RNAS, ribozymes, small interfering RNAs (RNAi) or aptamers that inhibit expression of myostatin or its receptor activin IIb. For example, an antisense RNA complementary to the translation initiation site of myostatin or activin IIb may be encoded by the rAAV genome. As another example, an RNA that binds to the myostatin or activin IIb double-stranded DNA may be encoded that prevents DNA unwinding and transcription. As yet another example, commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom siRNA molecules. In addition, commercially kits are available to produce custom siRNA molecules, such as SILENCER™ siRNA Construction Kit (Ambion Inc., Austin, Tex.) or psiRNA System (InvivoGen, San Diego, Calif.).

The rAAV genomes of the invention lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004).

In another aspect, the invention provides DNA plasmids comprising rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259: 4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871,982; and U.S. Pat. No. 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

In another aspect, the invention provides rAAV (i.e., infectious encapsidated rAAV particles) comprising a rAAV genome of the invention. Embodiments include, but are not limited to, the exemplified rAAV named "rAAV follistatin-344" and "rAAV MCK follistatin-344." The rAAV follistatin-344 genome includes in sequence an AAV2 ITR, the CMV promoter, an intron from the human β-globin gene, the follistatin DNA set out in SEQ ID NO: 11, a polyadenylation signal sequence from the human β-globin gene and another AAV2 ITR. The rAAV MCK follistatin-344 genome includes in sequence an AAV2 ITR, a truncated human muscle creatine kinase (MCK) promoter, a chimeric intron, the follistatin DNA set out in SEQ ID No: 11, the SV40 late polyadenylation signal and another AAV2 ITR. The chimeric intron is composed of the 5' donor site from the first intron of the human β-globin gene and the branchpoint and 3' splice acceptor site from the intron that is between the leader and the body of an immunoglobulin gene heavy chain variable region. The sequences of the donor and acceptor sites, along with the branchpoint site, have been changed to match the consensus sequences for splicing. The SV40 polyadenylation signal is used for efficient transcription termination. Both genomes lack AAV rep and cap DNA, that is, there is no AAV rep or cap DNA between the ITRs of the genome.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69 427-443 (2002); U.S. Pat. No. 6,566,118 and WO 98/09657.

In another embodiment, the invention contemplates compositions comprising rAAV of the present invention. These compositions may be used to enhance muscle and/or improve muscle function. In one embodiment, compositions of the invention comprise a rAAV encoding a myostatin inhibitor of interest. In other embodiments, compositions of the present invention may include two or more rAAV encoding different myostatin inhibitors of interest.

Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. Examples of disease states contemplated for treatment with methods of the invention are musculoskeletal diseases/disorders [for example, muscular dystrophies or inclusion body myositis (IBM)], neurodegenerative diseases/disorders in which muscle is adversely affected (for example, Amyotrophic Lateral Sclerosis multiple sclerosis and spinal muscular atrophy), sarcopenia, cachexia, obesity, Type II diabetes, Pompe disease and lysosomal storage disorders.

Combination therapies are also contemplated by the invention. Combination as used herein includes both simultaneous treatment or sequential treatments. Combinations of methods of the invention with standard medical treatments (e.g., corticosteroids for muscular dystrophies) are specifically contemplated, as are combinations with novel therapies. For example, for treatment of Muscular Dystrophies, methods of the invention may be combined with follistatin administration, followed by simultaneous or concomitant treatment to correct the genetic disorder. Correcting a genetic disorder may involve, for example, replacing sarcoglycans in sarcoglycan deficiency, correcting or replacing dystrophin in disorders such as Duchenne's Muscular Dystrophy, treating ALS patients with IGF-1 or mutant SOD1 interference strategies). Given that in disorder contemplated for treatment by the present invention, significant amount of muscle is lost, the prevention or rescue of muscle will give a substrate (preserved or regenerated muscle) for subsequent gene correction. In this respect, it may be conceivable to inhibit myostatin to enhance muscle, increase muscle size, and then provide the secondary treatment. Such secondary treatments for Muscular Dystrophy may be IGF-1, interfering RNA approaches, exon-skipping, calpain inhibition, dystrophin upregulation, and dystroglycan expression. Further, there may be additions to myostatin inhibition approaches to enhance the muscle boosting effects. For example, addition of IGF-1 or other trophic factors or muscle precursor injections could be performed. Myostatin inhibition in concert with muscle precursor cells (satellite cells, stem cells) may allow more of these cells to be incorporated into the tissue.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of rAAV (in particular, the AAV ITRs and capsid protein) of the invention may be chosen and/or matched by those skilled in the art taking into account the infection and/or disease state being treated and the target cells/tissue(s) that are to express the myostatin inhibitor protein(s).

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of myostatin inhibitors. The present invention thus provides methods of administering/delivering rAAV which express myostatin inhibitors to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., *Science*, 251: 761-766 (1991)], the myocyte-specific enhancer binding factor MEF-2 [Cserjesi and Olson, *Mol Cell Biol* 11: 4854-4862 (1991)], control elements derived from the human skeletal actin gene [Muscat et al., *Mol Cell Biol*, 7: 4089-4099 (1987)], the cardiac actin gene, muscle creatine kinase sequence elements [See Johnson et al., *Mol Cell Biol*, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypozia-inducible nuclear factors [Semenza et al., *Proc Natl Acad Sci USA*, 88: 5680-5684 (1991)], steroid-inducible elements and promoters including the glucocorticoid response element (GRE) [See Mader and White, *Proc. Natl. Acad. Sci. USA* 90: 5603-5607 (1993)], and other control elements.

Muscle tissue is an attractive target for in vivo gene delivery and gene therapy, because it is not a vital organ and is easy to access. The invention contemplates sustained expression of biologically active myostatin inhibitor proteins from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts. Since muscle tissue is readily accessible to the circulatory system, a protein produced and secreted by muscle cells and tissue in vivo will logically enter the bloodstream for systemic delivery, thereby providing sustained, therapeutic levels of protein secretion from muscle.

The term "transduction" is used to refer to the administration/delivery of myostatin inhibitor DNA to a recipient cell either in vivo or in vitro, via a replication-deficient rAAV of the invention resulting in expression of a functional myostatin inhibitor by the recipient cell.

Thus, the invention provides methods of administering an effective dose (or doses, administered essentially simultaneously or doses given at intervals) of rAAV that encode inhibitors of myostatin to a patient in need thereof.

BRIEF DESCRIPTION OF THE DRAWING

FIG. 1 demonstrates that AAV Follistatin induces gross body mass increase in mice.

FIG. 12 depicts histological examination of diaphragms at 10× from mdx animals stained with Masson's Trichrome.

FIG. 13 depicts histological examination of diaphragms at 20× from mdx animals stained with Masson's Trichrome.

FIG. 14 depicts histological examination of diaphragms at 40× from mdx animals stained with Masson's Trichrome.

FIG. 16 shows that follistatin-treated animals demonstrate higher numbers of revertant fibers in gastrocnemius.

EXAMPLES OF THE INVENTION

Figure 2:
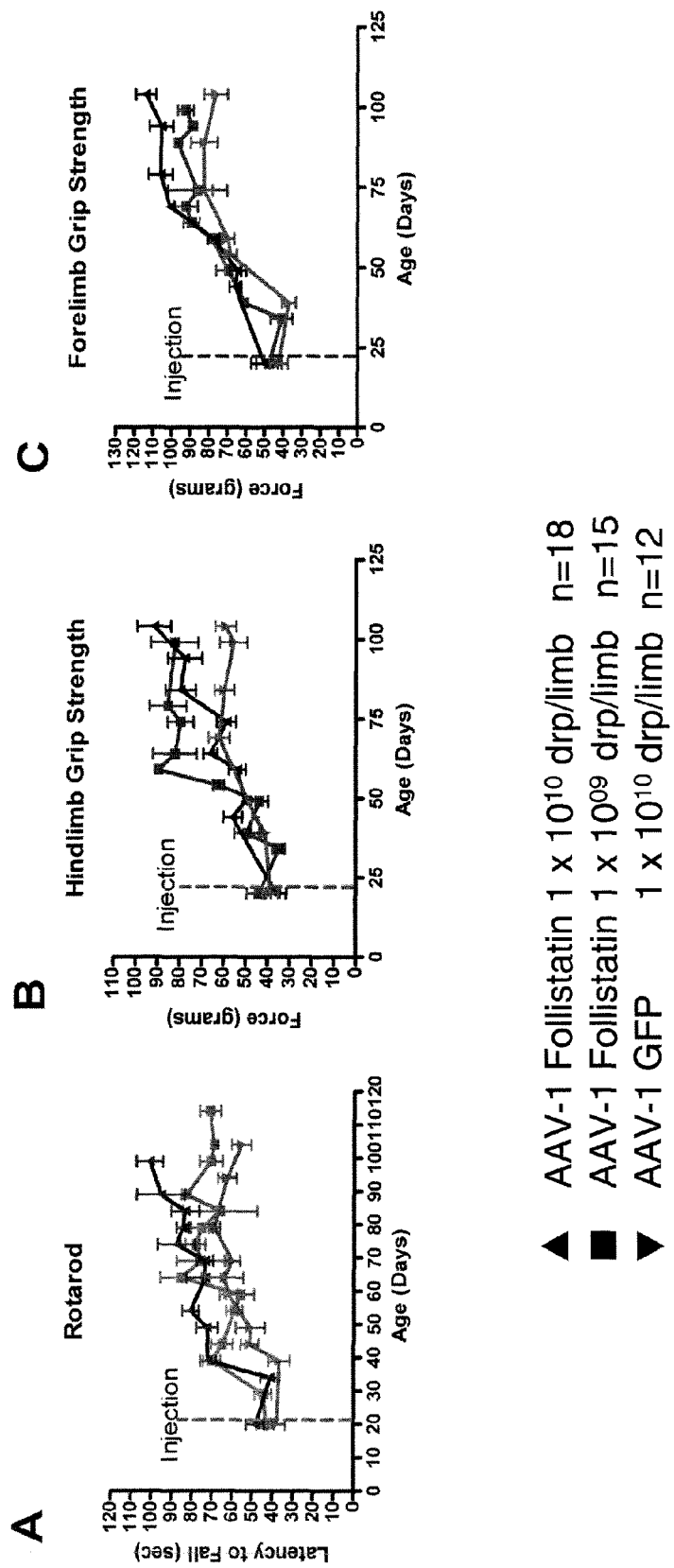
FIG. 2 depicts the dose response of AAV-Follistatin on motor function tests in mice.

Examples 1 and 2 below respectively describe the effect of a rAAV-delivered myostatin inhibitor in animal models of Limb-girdle muscular dystrophy Type 2D and Amyotrophic Lateral Sclerosis. Example 3 describes the effect of a rAAV-delivered myostatin inhibitor in the mdx animal model of muscular dystrophy. Example 4 describes a clinical protocol for treatment of inclusion body myositis with a rAAV-delivered myostatin inhibitor. Example 5 describes the effect of a rAAV-delivered myostatin inhibitor in wild type C57B1/6 mice. Example 6 describes the effect of a rAAV-delivered myostatin inhibitor in older mdx animals. Example 7 describes the effect of a rAAV-delivered myostatin inhibitor in non-human primates.

Example 1

Limb-girdle muscular dystrophy Type 2D (LGMD2D) is a debilitating disease of children and young adults. Caused by a mutation in any one of at least fifteen different genes, some types of LGMD2D are autosomal dominant and others are autosomal recessive. LGMD2D progresses slowly, resulting in weakness and wasting first of the muscles around the shoulders and hips (limb girdles) and sometimes later the muscles involved in cardiopulmonary function. To date, there is no proven treatment to delay the disease progression. Alpha-sarcoglycan knock-out mice are animal models for LGMD2D [Duclos et al., *J. Cell Biol.*, 142(6): 1461-1471 (1993)]. Experiments examining the effect of delivering follistatin using a rAAV are described below.

An AAV serotype 1 recombinant virus was constructed to encode a human follistatin DNA under the control of the strong human cytomegalovirus promoter. The rAAV was designated "rAAV follistatin UCSD". The human follistatin DNA (SEQ ID NO: 1) was a kind gift from Dr. Shumazaki (University of California-San Diego, La Jolla, Calif.). The amino acid sequence encoded by the DNA is set out in SEQ ID NO: 2. The DNA was subcloned into the EcoRI site of Bluescript containing a novel 5' Sfi I site and 3' Pme I site. The cDNA was then subcloned directionally into these sites of an AAV2-ITR-containing vector under the control of the human cytomegalovirus promoter [Kaspar et al., Mol Ther, 5: 50-56 (2002)]. Recombinant AAV-1 vectors were produced by triple transfection using calcium phosphate in human embryonic kidney carcinoma 293 cells (HEK-293). Briefly, a plasmid containing the Rep from serotype 2 and capsid from serotype 1 [Rabinowitz et al., J. Virol., 76: 791-801 (2002)] along with a helper adenoviral plasmid (Stratagene, Palo Alto, Calif.) was used. Transfected HEK293 cells were harvested 48 hours after transfection and resuspended in a small volume of 20 mM Tris (pH 8.0), 1 mM MgCl2 and 150 mM NaCl (T20MIN150). Cells were frozen and thawed four times and incubated with Benzonase (35 u/ml) for 30 minutes at 37° C. Cell debris were pelleted by centrifugation at 3,000 rpm at 40° C. for 15 minutes in a Beckmann GS-6R centrifuge. The cleared lysate was purified by a CsCl gradient purification process followed by anion exchange chromatography (PO-ROS HQ-50). A contract manufacturing company (Virapur LLC, San Diego, Calif.) was used for some virus preparations and titers confirmed. Titer was determined by QPCR techniques and titers were $3 \times 10^{12}$ DNase Resistant Particles (DRP)/ml.

To test myostatin inhibition in vivo, 4-8 week old male alpha-Sarcoglycan deficient mice were injected with a total of $1 \times 10^{10}$ DNase Resistant Particles of the rAAV follistatin UCSD or AAV-GFP (green fluorescent protein; control). The animals had been tested for baseline motor function at 3 weeks of age.

Gross body mass increases were seen in mice following administration of AAV-follistatin. (FIG. 1).

Motor functional tests included the accelerating Rotarod test and hindlimb and forelimb grip strength measurements (Columbus Instruments, Columbus, Ohio) (FIG. 2). Measurements were performed weekly (same day and time of each week). Each weekly session consisted of three trials on the elevated accelerating rotarod beginning at 4 rpm/min. The time each mouse remained on the rod was registered automatically. Grip strength meter testing was performed by allowing the animals to grasp a platform followed by pulling the animal until it release the platform, the force measurement recorded in four separate trials.

These motor function tests showed improvements in muscle strength in AAV-follistatin treated mice.

At 120 days, gross muscle evaluation and analysis of muscle weight, fiber number and cross-sectional area (CSA) on HE sections were performed as well as a follistatin ELISA assay. See Example 2 for procedures.

Figure 3:
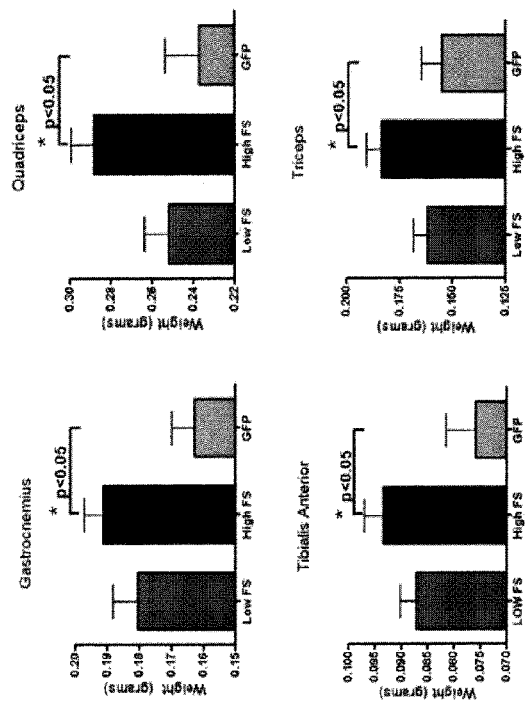
FIG. 3 shows that AAV-Follistatin induces muscle mass increase in mice.
Figure 4:
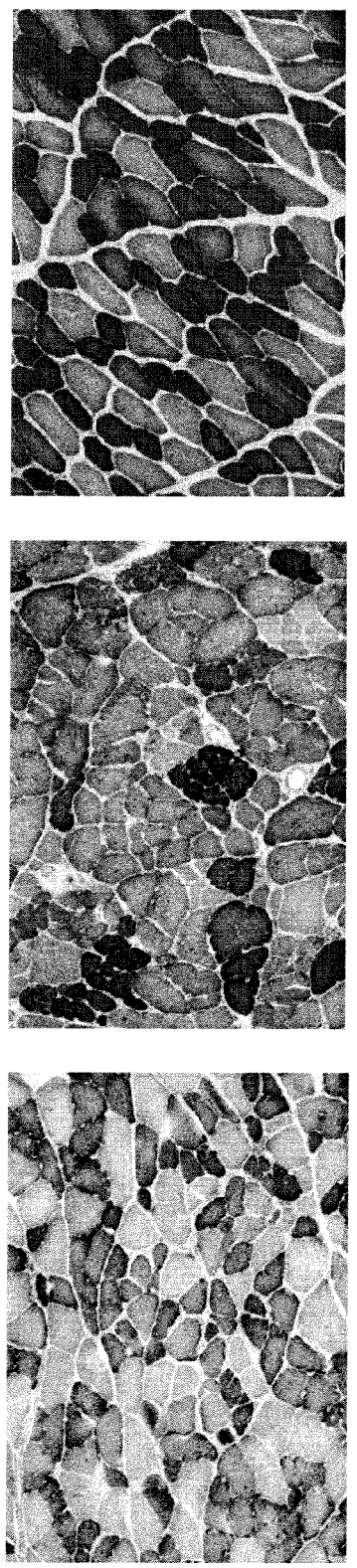
FIG. 4 depicts Succinate Dehydrogenase (SDH) staining on tibialis anterior and triceps muscles in mice.
Figure 5:
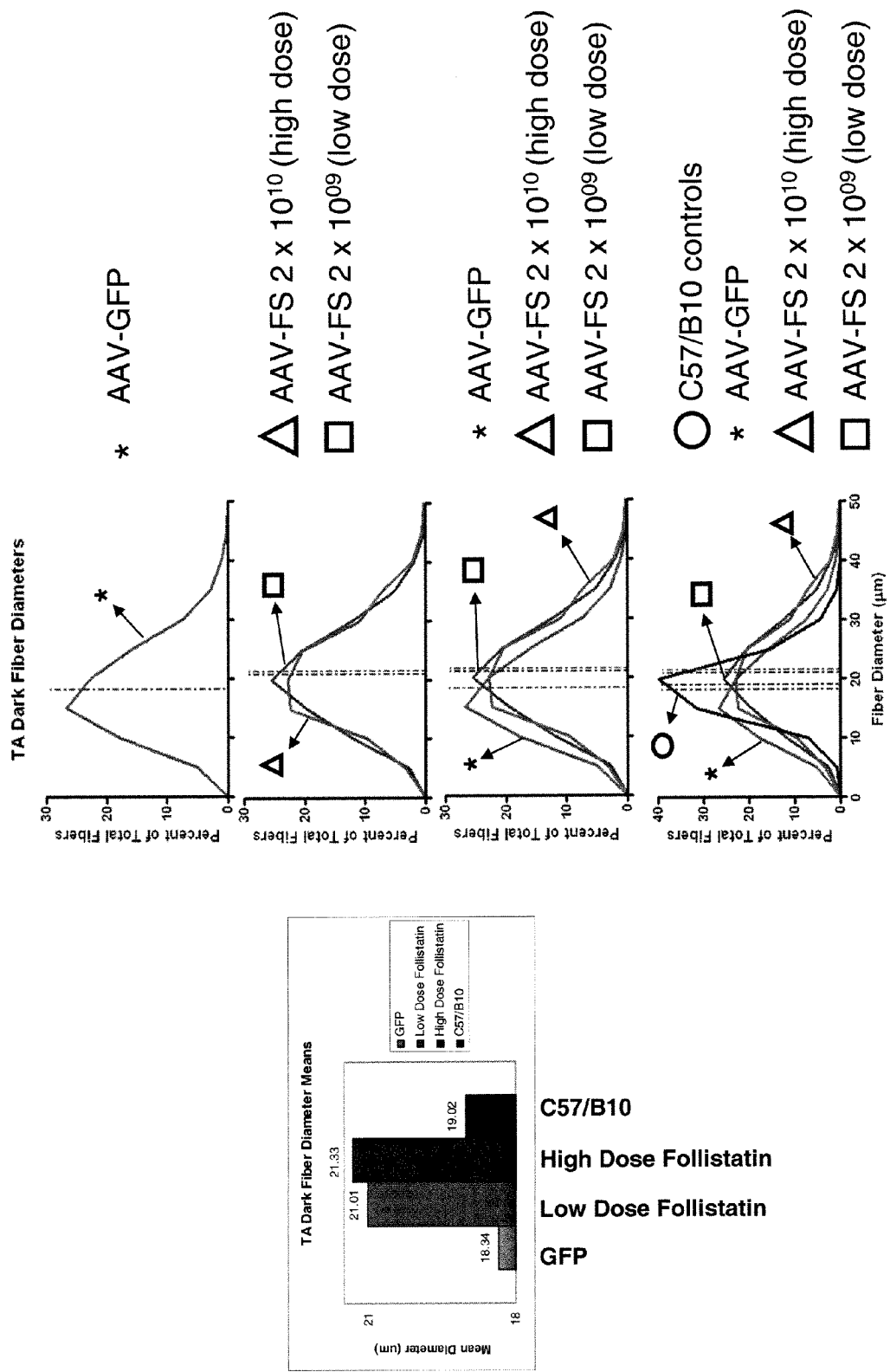
FIGS. 5-7 respectively represent the dark, intermediate and light tibialis anterior (TA) muscle fiber diameters that result from various doses of follistatin administration.
Figure 6:
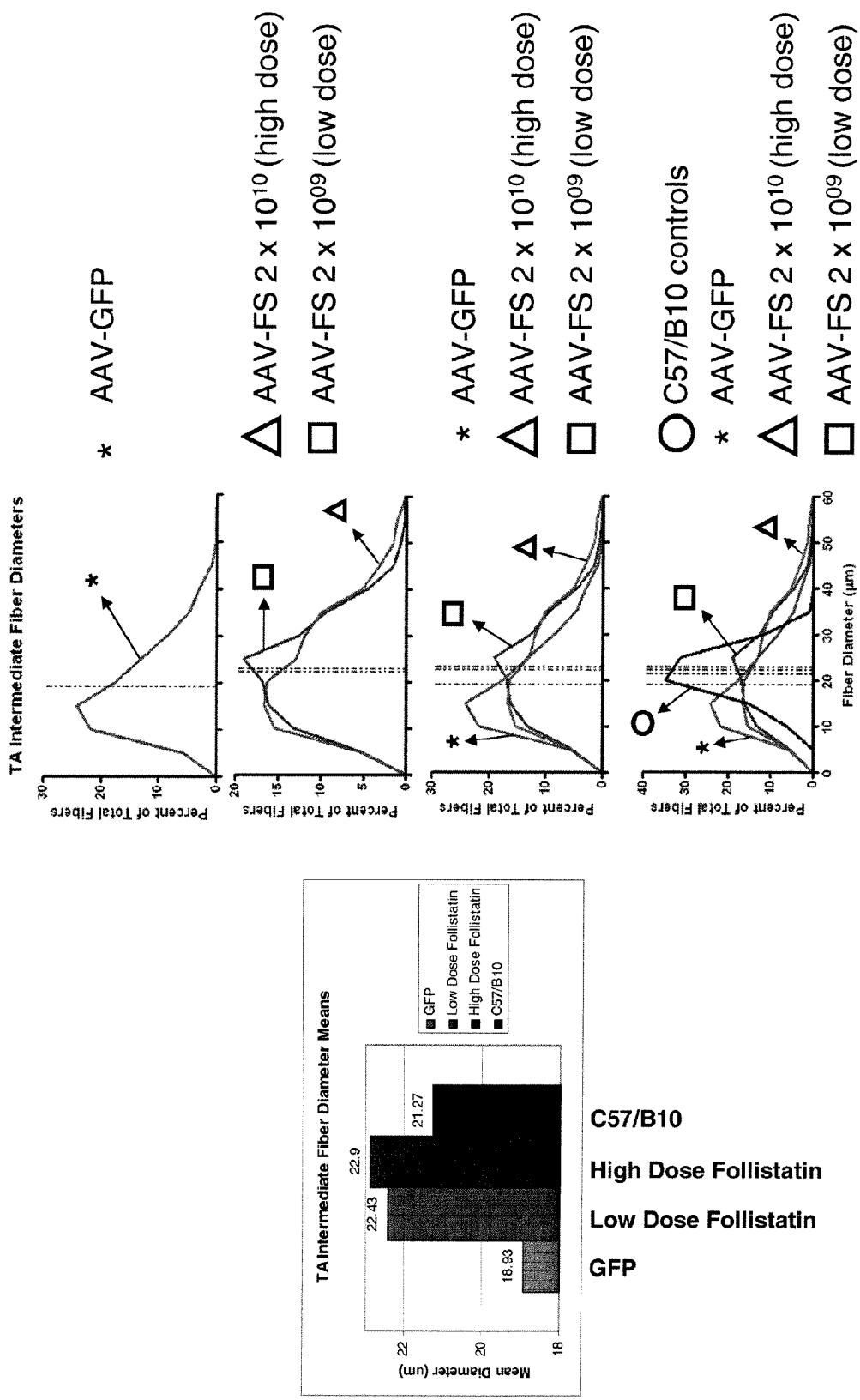
Figure 7:
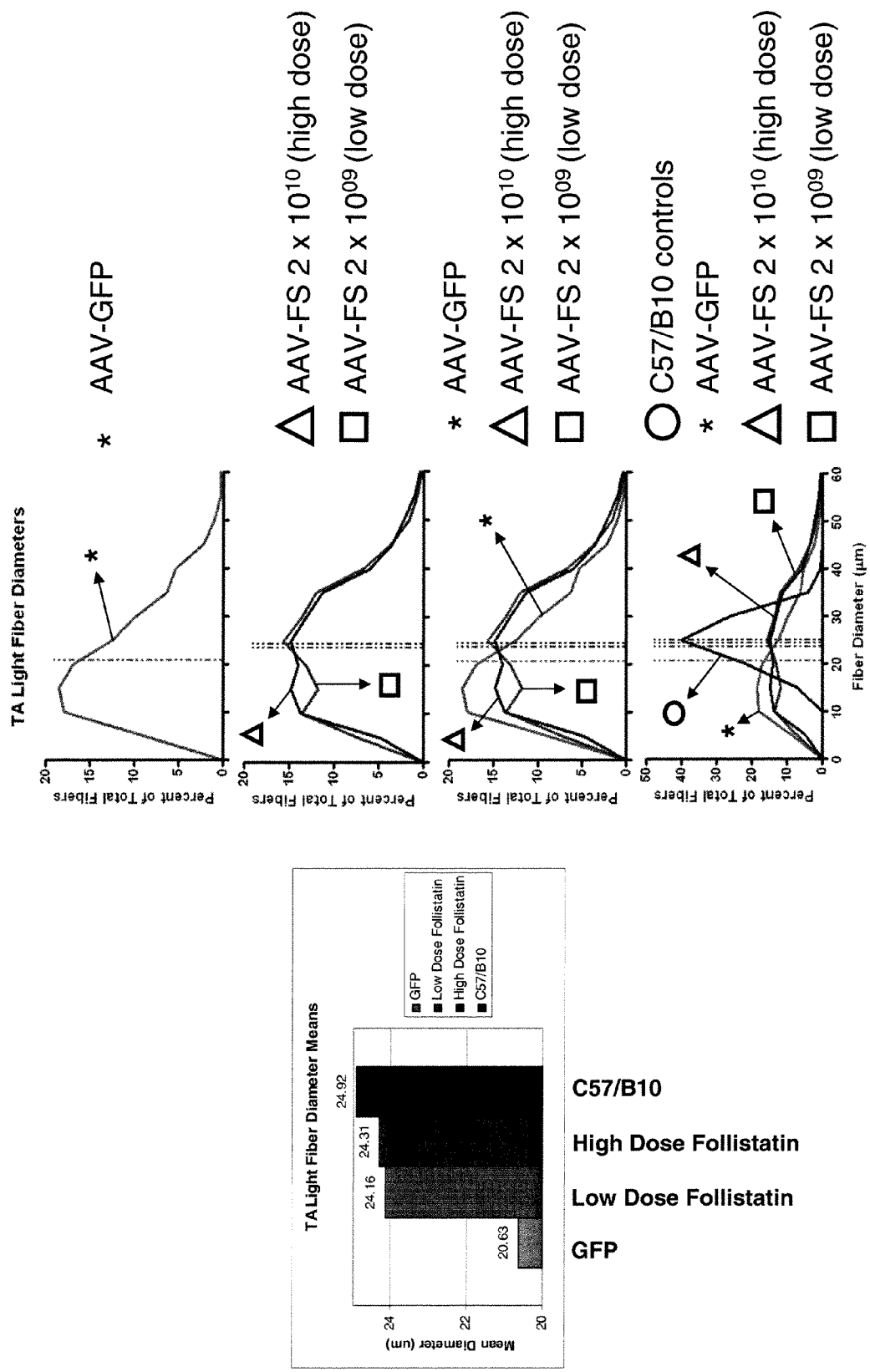
Figure 8:
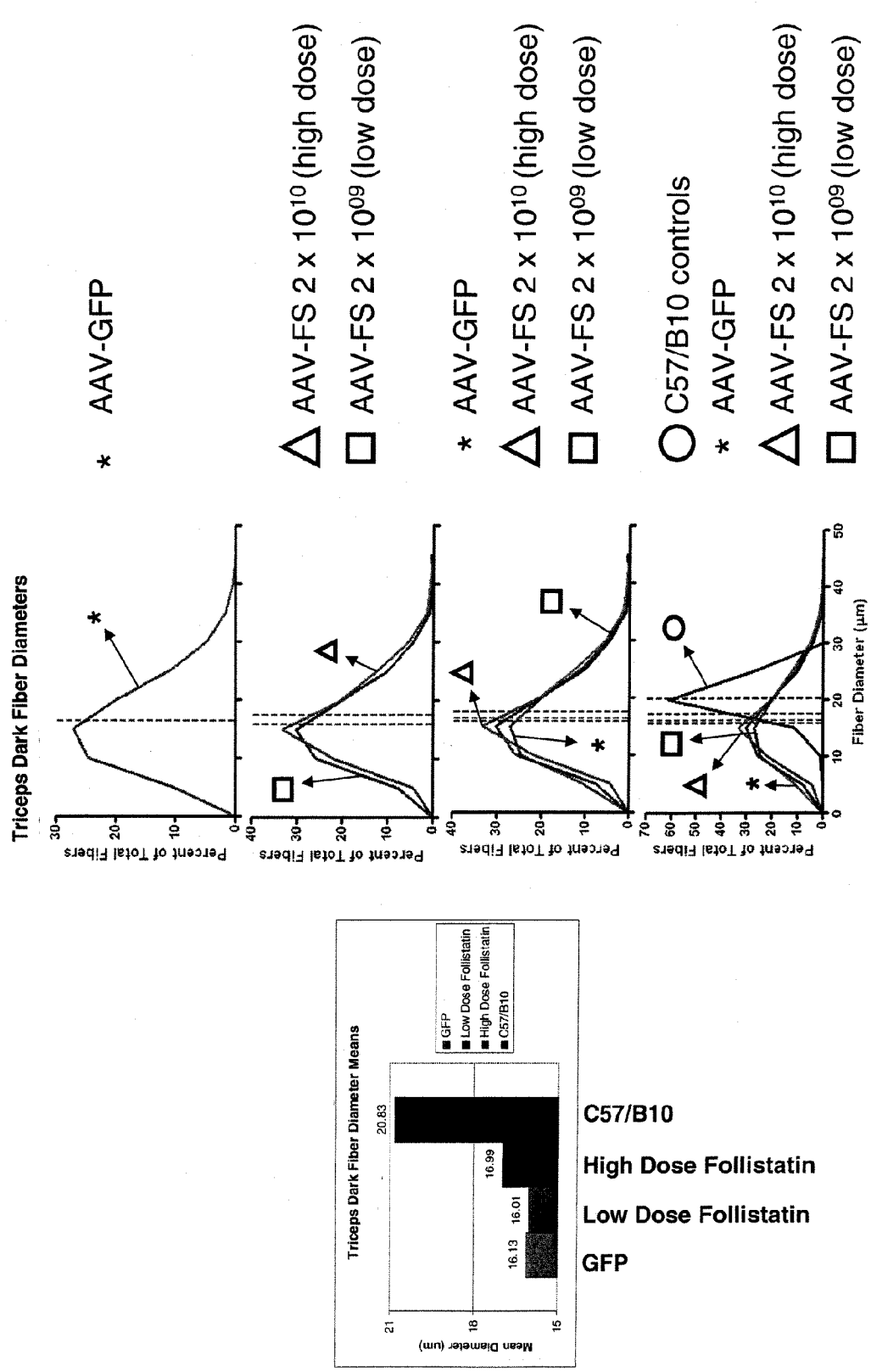
FIGS. 8-10 respectively represent the dark, intermediate and light tricep muscle fiber diameters that result from various doses of follistatin administration.
Figure 9:
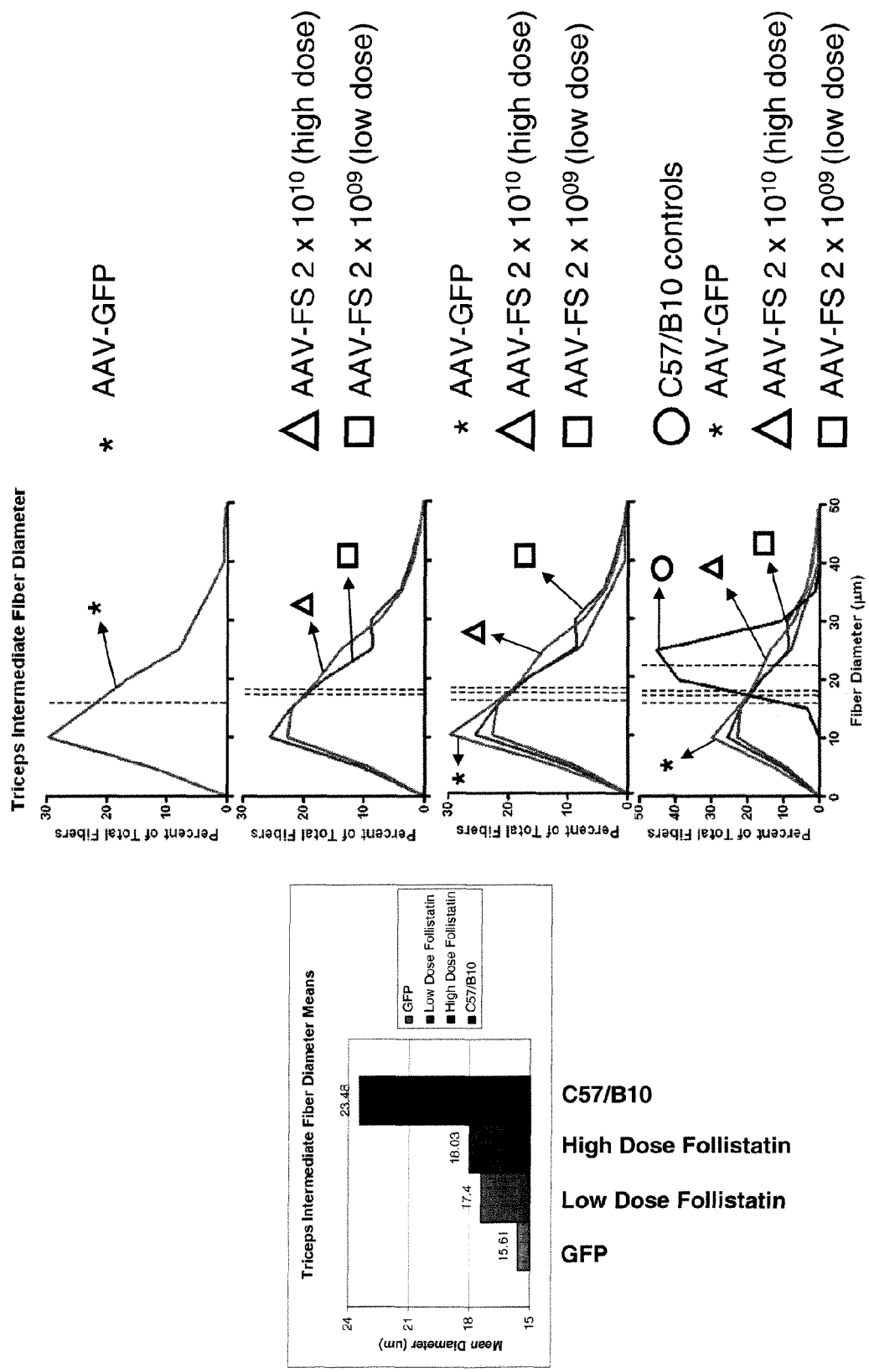
Figure 10:
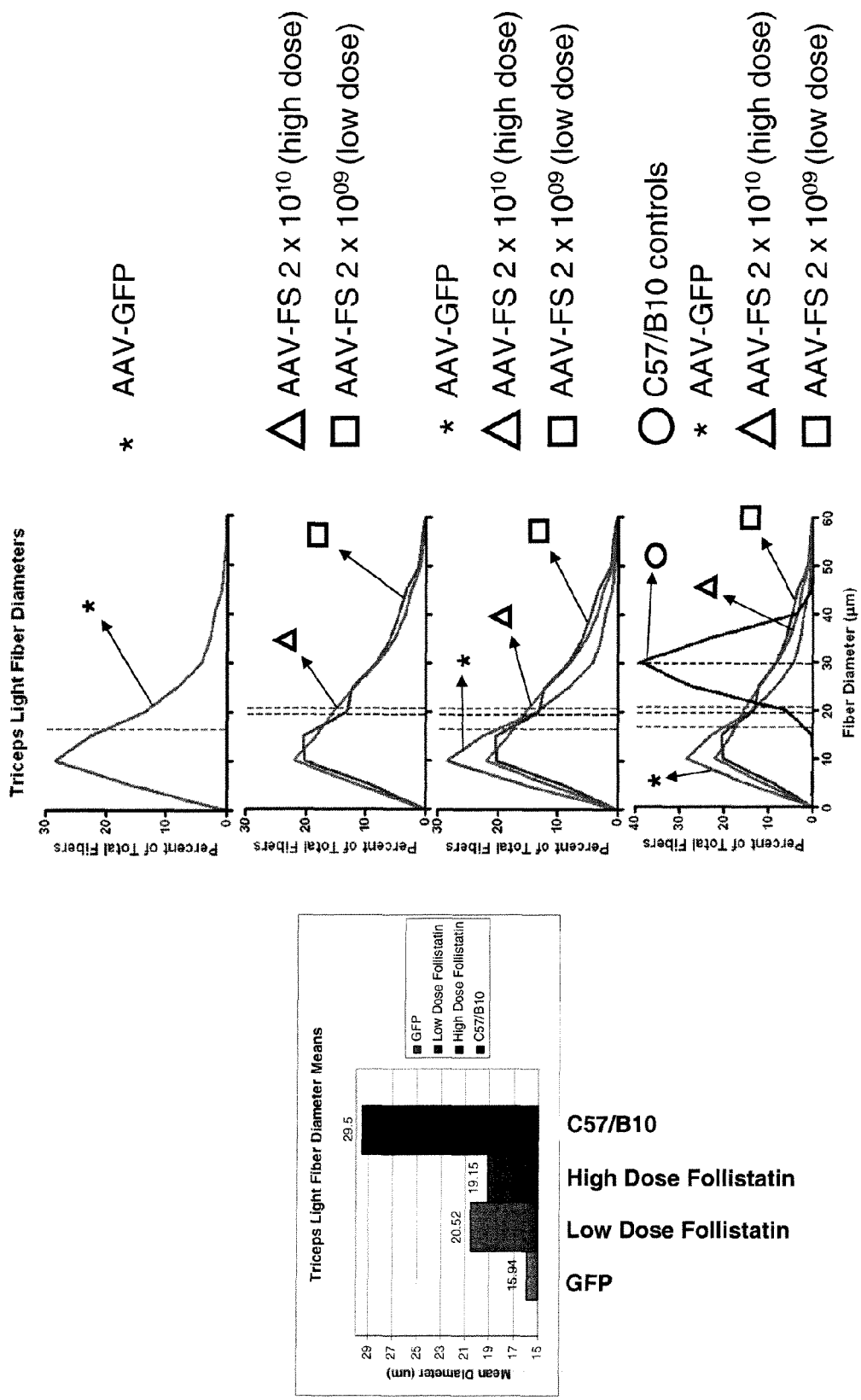

Increased serum follistatin levels accompanied by a local and remote increase in muscle mass were observed in rAAV-follistatin UCSD treated animals (p<0.05) (FIG. 3). Muscle hyperplasia was observed in comparison to controls. The number of central nucleated fibers was increased in AAV-follistatin treated animals indicating enhanced muscle regeneration. In addition, succinate dehydrogenase (SDH) staining was done on tibialis anterior (TA) muscle histological sections from control, treated, and wild type mice. SDH is a marker for oxidative, mitochondrial metabolism and classifies myofibers into oxidative or glycolytic fibers. This data supports a therapeutic effect of AAV-follistatin treatment in MD. This approach represents a clinically applicable gene delivery method to enhance muscle mass and function in LGMD2D with potential for treatment for other forms of MD.

Example 2

Amyotrophic Lateral Sclerosis (ALS), also known as Lou Gehrig's disease in the United States, is an adult onset disease that causes degeneration of motor neurons. The loss of motor neurons results in stiffness, atrophy of muscles, severe weakness of limb muscles, inability to walk, speak or swallow, and death two to five years after failure of the muscles that control respirations. Ten percent of ALS is familial and one fifth of these familial cases are caused by mutations in superoxide dismustase 1 (SOD 1). Transgenic mice and rats expressing a mutant human SOD1 transgene develop an ALS phenotype [Gurney et al., Science, 264: 1772-1775 (1994)]. Experiments examining effect of delivering follistatin using a rAAV are described below.

To test the ability for follistatin to reverse the myostatin-dependent inhibition on myoblast proliferation, C2C12 myoblasts were incubated with a growth inhibitory dose of myostatin (3 μg/ml) in the presence or absence of conditioned media from 293 cells infected with rAAV follistatin UCSD (described in Example 1) or conditioned media from cells infected with rAAV encoding Red Fluorescent Protein (RFP). The virus was produced as described for the AAV-follistatin in Example 1 except virus was collected 72 hours post-transfection and processed on cesium chloride gradients as previously described (Kaspar et al., 2002) C2C12 myoblasts were grown in DMEM (Invitrogen, Temecula, Calif.) containing 10% FBS (Invitrogen, Temecula, Calif.). Cell proliferation assays were conducted in a 96-well Nunc Microtiter plates and seeded at 1000 cells per well. After attachment, myostatin (R&D Systems) was added at a concentration of 3 μg/ml in the presence or absence of conditioned media. Conditioned media was created by infecting a well of 12 well dish with either 109 viral particles of AAV-Red Fluorescent Protein (RFP) or AAV-Follistatin (FS) and collecting the media 48 hours after infection. Three-days following myostatin inhibition, myoblast proliferation was assayed by the MTT assay. MTT proliferation assay was performed using a commercially available kit (Pierce Technologies). Data was collected in quadruplicate and read on a microplate reader set for absorbance at 570 nM. Results were presented as means and standard errors.

Myoblasts cultured in growth media steadily increased in cell number compared to myostatin-treated cultures, in which a significant decrease in proliferation was seen. Follistatin-conditioned media reversed the inhibition of proliferation by myostatin, whereas control RFP conditioned media did not.

To directly assess whether increased muscle proliferation affected disease course in a mouse model of inherited ALS caused by mutation in SOD1, rAAV follistatin UCSD or AAV-GFP (green fluorescent protein; control) ($1 \times 10^{10}$ viral genomes per injection) were injected bilaterally via intramuscular delivery into the hindlimb quadriceps and tibialis muscles of 16 mice each at 40 days of age (equal distribution of male and female animals).

Mice were observed daily for survival. Survival analysis was performed by Kaplan-Meier analysis which generates a $\chi 2$ value to test for significance. The Kaplan-Meier test was performed using the log-rank test equivalent to the Mantel-Haenszel test. In addition, two tailed p values were calculated. When comparing survival curves, median survival times were calculated with a 95% confidence interval. All other statistical tests not involved in survival analysis were performed by multi-way analysis of variance followed by a Bonferroni post hoc analysis of means differences between groups (GraphPad Prizm Software, San Diego, Calif.). Testing of motor function using a rotarod device (Columbus Instruments, Columbus, Ohio) began at 35-40 days of age. Each weekly session consisted of three trials on the elevated accelerating rotarod beginning at 5 rpm/min. The time each mouse remained on the rod was registered. Grip Strength measurements for forelimb and hindlimbs were tested weekly using a grip strength meter (Columbus Instruments, Columbus, Ohio). Each weekly session consisted of 4 tests per animal per limb. To determine mortality in a reliable and humane fashion, we used an artificial end point, defined by the inability of mice to right themselves 30 seconds after being placed on their sides. The moribund mice were scored as "dead" and were euthanized, and tissues were collected.

Both sets of animals reached end stage disease at ~126 days. Despite this, follistatin treated muscles showed gross changes including widespread increased muscle mass in compared to the GFP treated animals. Easily seen from visual inspection, wet weights of multiple muscles (n=10-15 animals each), including the tibialis anterior, gastrocnemius, medial quadriceps and triceps muscles were significantly ($p<0.05$) after injection of AAV-follistatin. Increased muscle mass was not limited to the hindlimb muscles injected. Using a commercially available ELISA assay (R & D Systems) specific for human follistatin, circulating blood levels of follistatin were found to be significantly elevated (>10 ng/ml) at 100 days of age of AAV-follistatin treated animals, but not AAV-GFP animals, indicating that follistatin was acting in a paracrine manner on all skeletal muscles. Data was collected in triplicate for each animal and presented as means with standard error.

To determine whether the muscle weight increase was due to hyperplasia, hypertrophy and/or muscle sparing in the ALS animals, skeletal muscle hypertrophy and myofiber number were investigated. Muscles were embedded in Optimal Cutting Temperature Compound (OCT) and snap frozen in liquid nitrogen cooled isopentane. Transverse 10 μm sections were cut through the middle of the muscle and sections stained with H & E and trichrome stains. The sections (4 sections each animal) were photographed on a Zeiss Axiovert microscope connected to a Zeiss micrometer on a Dell Workstation. The total area of the muscle cross section was calculated and individual myofibers were counted and diameters measured. Graphs of total fiber numbers per section and a percentage of fiber diameters were plotted (FIGS. 5-10).

Figure 11:
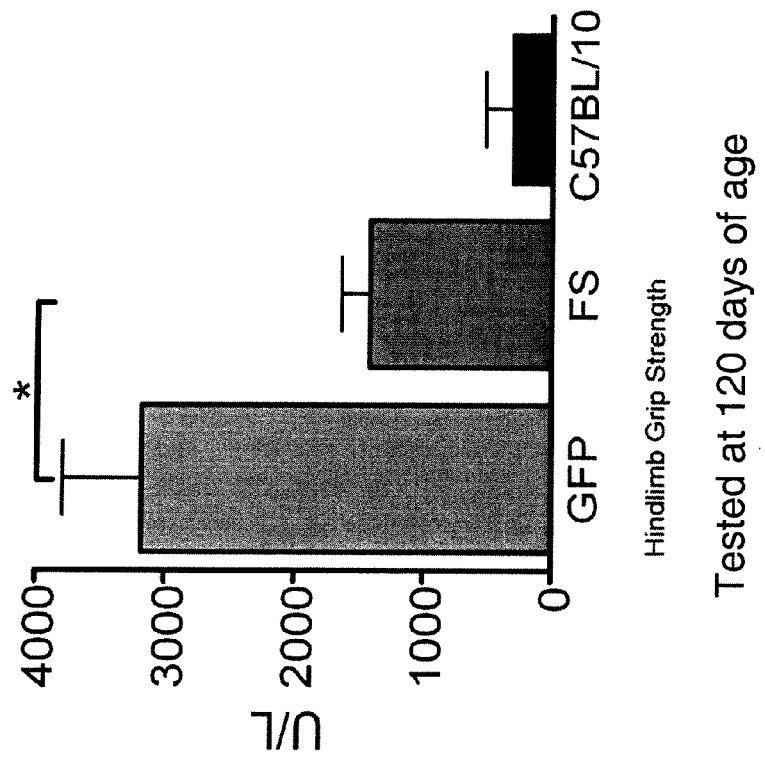
FIG. 11 demonstrates that follistatin treatment attenuates the levels of serum creatine kinase.
Figure 15:
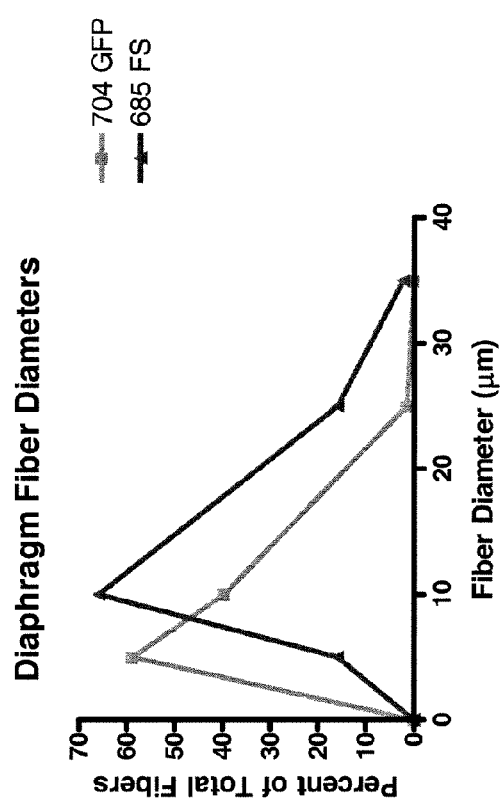
FIG. 15 shows that follistatin induces hypertrophy in diaphragm muscle fibers.

This revealed that at end stage (126-127 days) approximately 2 fold more myofibers were present in the gastrocnemius compared to GFP-treated animals (n=8 animals) ($p<0.01$). Follistatin treated muscles were also slightly hypertrophic based on measurements of myofiber diameters in the quadriceps and gastrocnemius muscles compared to AAV-GFP treated animals. Moreover, serum creatine kinase levels were decreased in AAV-follistatin treated animals versus AAV-GFP treated animals (FIG. 11).

Increased muscle mass, increased myofiber number, and hypertrophy of muscle fibers translated, as expected, into increased strength in the follistatin-treated animals. By 75 days of age, follistatin-treated animals showed a 40% increase in hindlimb strength compared with GFP treated littermates, remaining comparable to the non-transgenic animals at 75 days. Strength in the forelimbs was also increased from 60-120 days of age or end-stage. The increased strength did not afford these mice better performance with other measures, including a rotarod test, presumably reflecting that strength is only one measure of performance in this particular test. Despite maintenance of muscle strength and increased muscle mass even through end stage, no statistically significant increase in survival (defined by paralysis so severe that the animal was unable to right itself within 30 seconds) was seen in the follistatin-treated mice versus untreated or AAV GFP treated cohorts (AAV-GFP 126, AAV-Follistatin 130; p value 0.06, Chi Square 3.504).

Enhancement of muscle mass and prevention of muscle atrophy by inhibition of myostatin with virally delivered follistatin yielded the expected increase in muscle mass and delayed atrophy. It is contemplated that this result will translate into therapeutic benefit in human patients treated with a myostatin inhibitor of the invention.

Example 3

Another AAV serotype 1 recombinant virus was constructed to encode a human follistatin DNA under the control of the strong human cytomegalovirus promoter. The rAAV was designated "rAAV follistatin-344". The DNA and amino acid sequences of the follistatin encoded are respectively set out in SEQ ID NOs: 11 and 12. The rAAV follistatin-344 was administered to mdx mice (Bogdanovich et al., supra) which are an animal model of MD.

Eighteen three-week old mice were injected with $1 \times 10^{10}$ drp/limb of the rAAV while fifteen three-week old mice received $1 \times 10^9$ drp/limb. Twelve other mice received $1 \times 10^{10}$ drp/limb AAV-GFP. Results of the treatment are presented in FIGS. 1 through 17.

Treatment with rAAV follistatin-344 resulted in muscle enhancement and improved muscle function in the treated animals and it is contemplated that these results will translate into therapeutic benefit in human MD patients treated with a myostatin inhibitor of the invention.

Example 4

Inclusion body myositis (IBM) is an inflammatory muscle disease characterized by progressive muscle weakness and wasting. The disorder is similar to another inflammatory myopathy called polymyositis. IBM is often the diagnosis for cases of polymyositis that are unresponsive to therapy, but IBM has its own distinctive features. The onset of muscle weakness in IBM is generally gradual (over months or years). Falling and tripping are usually the first noticeable symptoms. For some patients the disorder begins with weakness in the hands causing difficulty with gripping, pinching, and buttoning. IBM occurs more frequently in men than in women and affects both the proximal (closest to the center of the body) and distal (farthest from the center of the body) muscles. There may be weakness of the wrist and finger muscles and atrophy of the quadricep muscles in the legs. Atrophy or shrinking of the forearms is also characteristic. Difficulty swallowing (dysphagia) occurs in approximately half of IBM cases. Symptoms of the disease usually begin after the age of 50, although the disease can occur earlier. IBM is generally resistant to all therapies, and its rate of progression appears to be unaffected by any currently available treatments.

It is contemplated that muscle enhancement and particularly quadriceps muscle enhancement will benefit patients suffering from sporadic IBM (sIBM). Enhancement of muscle and/or improved muscle function resulting from delivering follistatin using a rAAV may be confirmed as described below where methods of treatment of mdx mice and sIBM human patients are set out.

Treatment of Mdx Mice

C57B1/10 (wild-type) and mdx animals (Bogdanovich et al., supra) receive bilateral injections using a 26 gauge Hamilton needle of rAAV follistatin-344 into the quadriceps at 3 weeks of age (n=8 animals/dosage/vector). Four doses are tested, $1\times10^{11}$, $1\times10^{10}$, $1\times10^{9}$, $1\times10^{8}$ viral particles per quadriceps. One group of animals (n=8) will be injected with AAV.CMV.GFP (rAAV comprising DNA encoding green fluorescent protein linked to the CMV promoter) as a control using the high dosage; $1\times10^{11}$ viral particles. Tacrolimus and MMF were given daily to animals 1 week prior to viral delivery and for 8 weeks following viral gene delivery. Doses were based on comparable schedules to patient dosing (0.2 mg/kg tacrolimus and 25 mg/kg MMF).

Levels of follistatin were measured monthly. Blood was collected by retro-orbital eye bleeds (routinely performed in our lab) and serum separated in serum-separator tubes. A commercially available ELISA assay kit specific for human follistatin is available (R&D Systems) and may be used to detect follistatin. Animals were sacrificed at 4 months of age. The quadriceps, tibialis anterior, extensor digitorum longus muscles, gastrocnemius, soleus, plantaris, diaphragm and biceps femoris muscles were dissected from each side of the animals. Muscles were mounted and snap frozen in liquid nitrogen-cooled isopentane, and cross-sectioned at 8-12 µm on a cryostat at −18-20° C. followed by histopathology stains (trichrome and H&E). To distinguish between hypertrophy and hyperplasia, morphometric examination of the muscles was performed using systematic sampling of unbiased counting frames using a semi-automatic stereology system and morphometric analysis will be performed using Metamorph. Pathologic irregularities including fibrosis, inflammation and cytoplasmic bodies were noted (FIGS. 12-14). Muscle hypertrophy was noted in those animals receiving follistatin treatment (FIG. 15), and they also produce higher numbers of revertant fibers in gastrocnemius muscle (FIG. 16).

Figure 17:
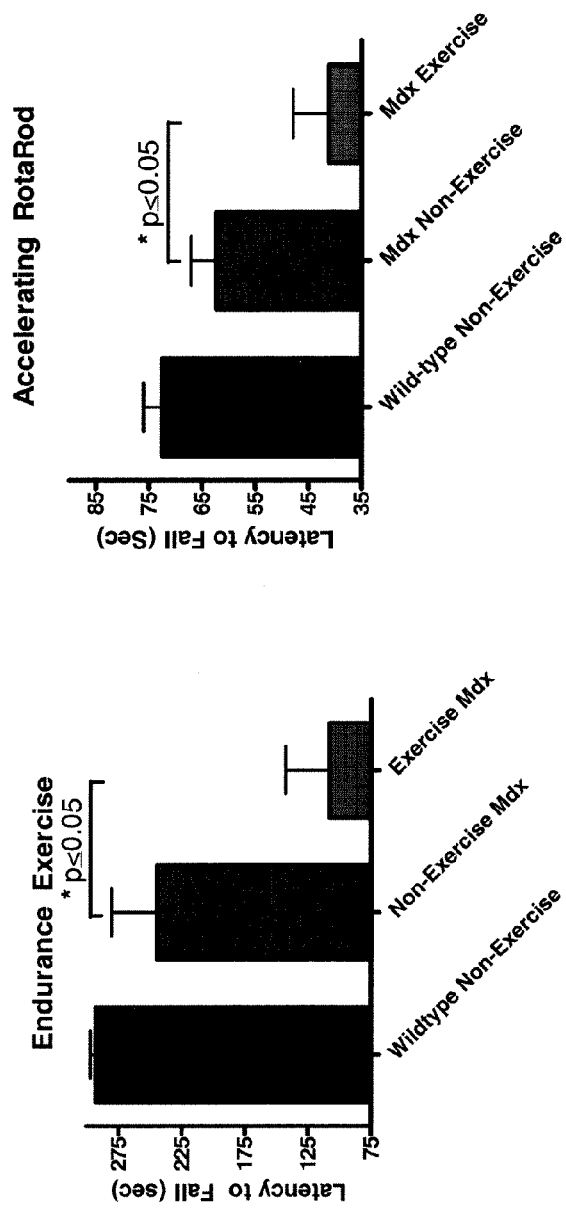
FIG. 17 depicts studies done to assess muscle function of 8-week old animals that were forced to exercise daily on a treadmill for 12 weeks.

Exercise studies done on 8-week old mdx animals that were treated with AAV-follistatin were compared to non-exercised animals as well as wild type non-exercised animals. The results show that administration of AAV-follistatin mice could perform better than both the non-exercised mdx and non-exercised wild type mice in endurance as well as accelerating RotaRod tests (FIG. 17).

rAAV1-follistatin virus is produced in 293 cells by calcium phosphate transient transfection using the AAV vector plasmid containing the AAV1 inverted terminal repeats and using pXR1 helper plasmid providing rep and cap serotype 1 in trans, and pHelper-Adenoviral plasmid [Xiao and Samulski, *J. Virol.*, 72(3): 2224-2232 (1998)]. Three days following transfection, cells are harvested, freeze thawed and purified by cesium chloride density gradient ultracentrifugation. Fractions containing virus are dialyzed against Hepes buffered saline. Determination of viral titer was determined using real time quantitative PCR as well as functional testing of transgene expression by limiting dilutions of virus on 293 cells using immunohistochemistry.

Statistical Analysis: Statistical analysis was performed by multi-way ANOVA followed by a Bonferroni post-hoc analysis of means differences between groups (InStat and GraphPad Software).

Treatment of sIBM Human Patients

Patients receive an immunosuppression regimen of tacrolimus and MMF during the study period. One group of patients is injected in the quadriceps with rAAV follistatin-344 and the other group receives sham injections, Since the patients in the trial will receive an immunosuppression regimen that could influence their course, at minimum a separate group receiving tacrolimus and MMF should be treated to distinguish the effects of the drug regimen from gene transfer.

Six sIBM patients will be included based on the following criteria. Subjects must fulfill the following characteristic features of sIBM a) duration of illness>6 months, b) age of onset>30 yrs; c) quadriceps muscle strength must be in the MRC grade 4 range; d) muscle biopsy proven diagnosis of IBM: (including mononuclear cell inflammation, vacuolated muscle fibers and either intracellular amyloid deposits or 15-18 nm tubulofilaments by EM). Sexually active patients must also be willing to practice a reliable method of contraception during the study. Exclusion Criteria will be active viral infection, concomitant illness or requirement for chronic drug treatment that in the opinion of the PI creates unnecessary risks for gene transfer or conflicts with immunosuppressive regimen and pregnant women Dose escalation study of rAAV1 carrying the human follistatin gene under control of the CMV promoter (rAAV follistatin-344) given as a multiple intramuscular injections to the quadriceps muscles on both sides. The planned dose for cohort 1 (three patients) will be $3\times10^{12}$ [in six divided quadriceps muscle injections of $2.5\times10^{11}$ viral genomes (vg)] followed by cohort 2 receiving $3\times10^{13}$ (in six divided quadriceps muscle injections of $2.5\times10^{12}$ vg). Patients will be injected at six week intervals. Patients will receive tacrolimus (0.2 mg) and mycophenolate mofetil (1 g BID) daily starting one week prior to gene transfer and drug will continue for at least six months post gene transfer. Patients may opt to continue the drug depending on the discretion of the principal investigator. At minimum a separate, parallel group of IBM patients will receive immunosuppression using tacrolimus and MMF will be compared to the gene transfer cohort.

Baseline measures to be taken prior to injection (day −7 to day −1) are quantitative muscle testing (Maximum voluntary isometric contractions or MVICT) to measure quadriceps (knee extensors) muscle strength and hand strength will be assessed with a grip dynamometer. MVICT on additional muscles including elbow flexion and extension and knee flexion are also obtained. These will be the muscles used to evaluate strength following gene transfer. Functional testing will include time to climb four standard steps, time to walk 30 feet, and time to get up from a chair. Baseline laboratory work will include CBC, platelets, blood urea nitrogen (BUN), GGT, bilirubin, alkaline phosphatase, creatinine, amylase, serum protein electrophoresis, protime, and PTT, neutralizing antibodies to AAV and western blot detection of antibodies to follistatin. Patients will require hepatitis screening, chest x-ray, echocardiogram, and EKG. Females of childbearing potential will have a pregnancy test. Adult males will be asked to provide a semen sample.

Patients will return to a designated monitored bed following gene transfer and vital signs will be obtained hourly for four hours following the injection and then every 4 hours for 3 days prior to discharge. Patients will return for follow up visits on days 7, 14, 30, 60, and 90. Muscle biopsies will be performed on both quadriceps muscles on day 90. Blood will be taken for neutralizing antibody to AAV1, and antibody to follistatin at each visit. In addition, ELISpots will be performed using capsid peptides to establish T cell responses to rAAV1 and follistatin. On days 14, 30, 60, and 90, a more comprehensive battery of tests will include GGT, bilirubin, BUN, alkaline phosphatase, creatinine, CBC, platelets, amylase, cholesterol, triglycerides. Semen samples will be requested on days 60 and 90. Muscle will be studied using multiple serial sections. For leukocyte markers (CD45, CD3, CD4, CD8, MAC 387). Muscle will also be examined for histological appearance using modified trichrome, H & E, oxidative enzymes, and ATPase. Muscle sections will also be pooled for PCR analysis for viral DNA. Patients will be followed for every six months for two years.

Muscle strength based on MVICT of each individual muscle including quadriceps, knee extensors, elbow extensors, and elbow flexors and hand grip dynamometer will be performed prior to gene transfer and at six months (completion of study). The best of three measures at each of these time points will be used for analysis. An intermediate time point will be obtained at 3 months but used only to evaluate as a safety measure in case of adverse effects of the gene transfer. Muscle biopsy will be performed on both quadriceps post gene transfer. This muscle will not undergo biopsy pre-gene transfer for a variety of reasons. First, it will be too invasive to do biopsies on both quadriceps muscles before and after. The post gene transfer biopsy at six months will be necessary to establish the size of individual muscle fibers and degree of inflammation. Fiber size distribution histograms (#/mm2) will be obtained from 5 randomly selected areas of the removed muscle (one central and four peripheral). In addition, fiber type histograms will be analyzed separately to determine if there is a preferential effect. Muscle will also be analyzed for number and distribution of T and B cells and macrophages, number of internal nuclei, number of muscle fibers undergoing necrosis, and number of regenerating muscle fibers. Vector titers in the muscle will be determined in the tissue by quantitative PCR.

Outcome variables will include changes from baseline to 6 months with a two-way analysis of variance model with 24-week change from baseline as the dependent variable and treatment group as the independent variable. An F test will be performed for significance of the difference in the adjusted treatment group means, and a 95% CI for the difference will be constructed. This analysis will apply mainly to MVICT but will also be applied to variables in the muscle biopsies between treatment groups.

Example 5

Figure 18:
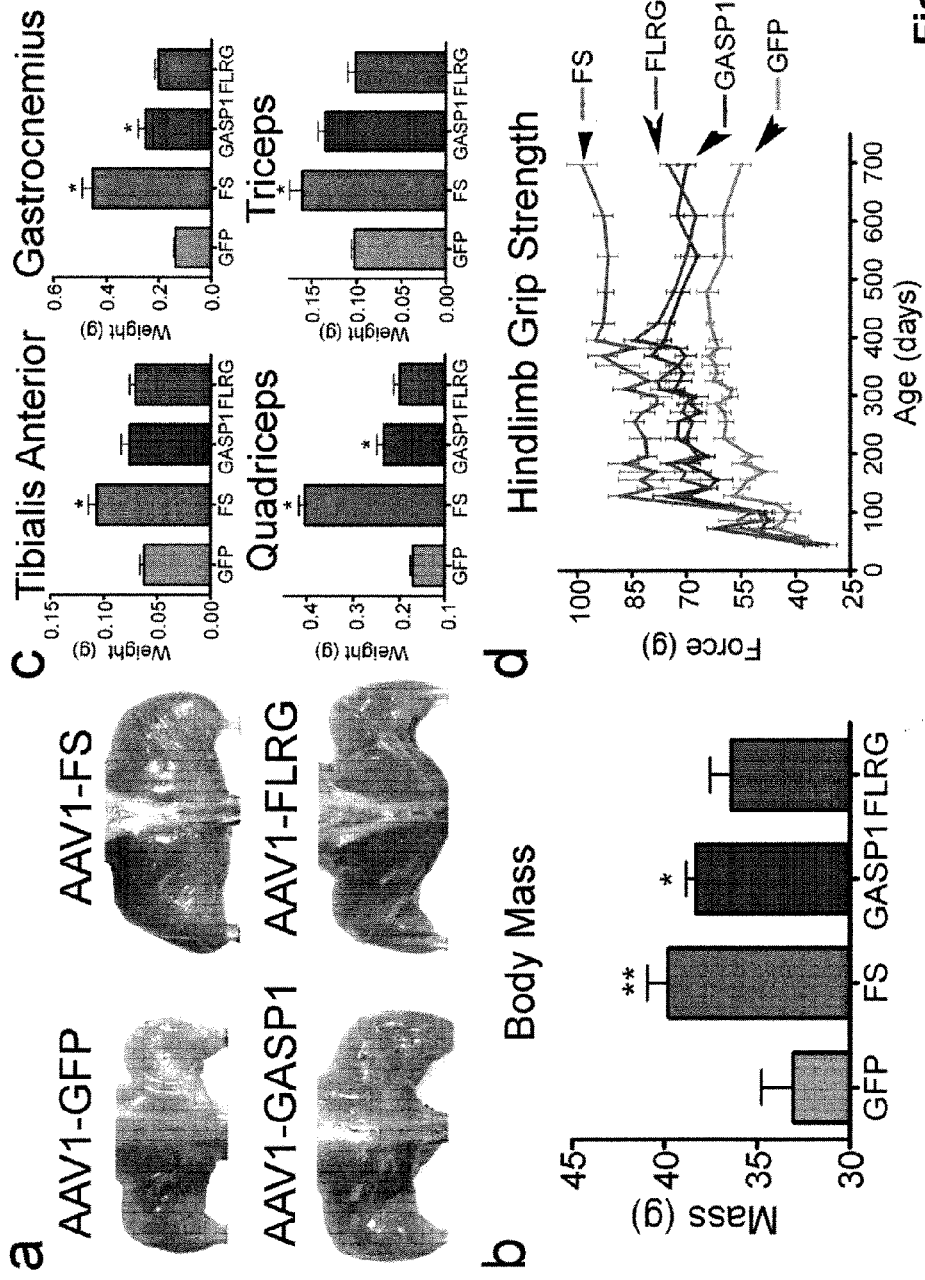
FIG. 18 demonstrates that myostatin inhibitor proteins can increase muscle mass and strength in wild type C57BL/6 mice.

To demonstrate the effect of AAV delivery of various myostatin inhibitors in vivo, mice were treated with AAV1 according to the present invention. Briefly, $1 \times 10^{11}$ AAV1 viral particles were administered per animal. Recombinant AAV administered were: rAAV follistatin-344, rAAV encoding FLRG, rAAV encoding GASP-1, or rAAV encoding GFP. The DNA and amino acid sequences of FLRG are respectively set out in SEQ ID NOs: 7 and 8 while the DNA and amino acid sequences of GASP-1 are respectively set out in SEQ ID NOs: 9 and 10. The rAAV were administered bilaterally into the quadriceps and tibialis anterior muscles of 4-week-old wild-type C57Bl/6 mice. Results are presented in FIG. 18.

All animals treated with the myostatin inhibitors demonstrated an increase in body mass with an observable gross enhancement of muscles when analyzed at 725-days of age compared to GFP-treated controls (FIG. 18a,b). Evaluation of individual muscle weights showed an increase in muscle mass for all myostatin inhibitor-treated animals, with the greatest increase in FS-treated animals compared to GFP controls. The increased muscle mass was found in the injected hindlimb muscles as well as remote muscles to the injection site, such as the triceps. Thus, these inhibitors were secreted into the circulation from the site of muscle injection, enhancing skeletal muscle mass at remote sites (FIG. 18c). The enlarged muscle mass was accompanied by functional improvement demonstrated by an increase in hindlimb grip strength (FIG. 18d). There was no effect on heart mass or histological appearance of cardiomyocytes, indicating that myostatin inhibition was selective to skeletal muscle tissue (data not shown). No change in reproductive capacity in mice treated with rAAV follistatin-344 was found. Furthermore, no histological/pathological alterations in the gonadal tissue of rAAV follistatin-344-treated mice was seen compared to controls (data not shown).

The results discussed above demonstrate that administration of AAV encoding myostatin inhibitors according to the invention enhances muscle and improves muscle function in vivo.

Example 6

The ability of rAAV follistain-344 to increase muscle strength in older mdx animals was also examined.

Figure 19:
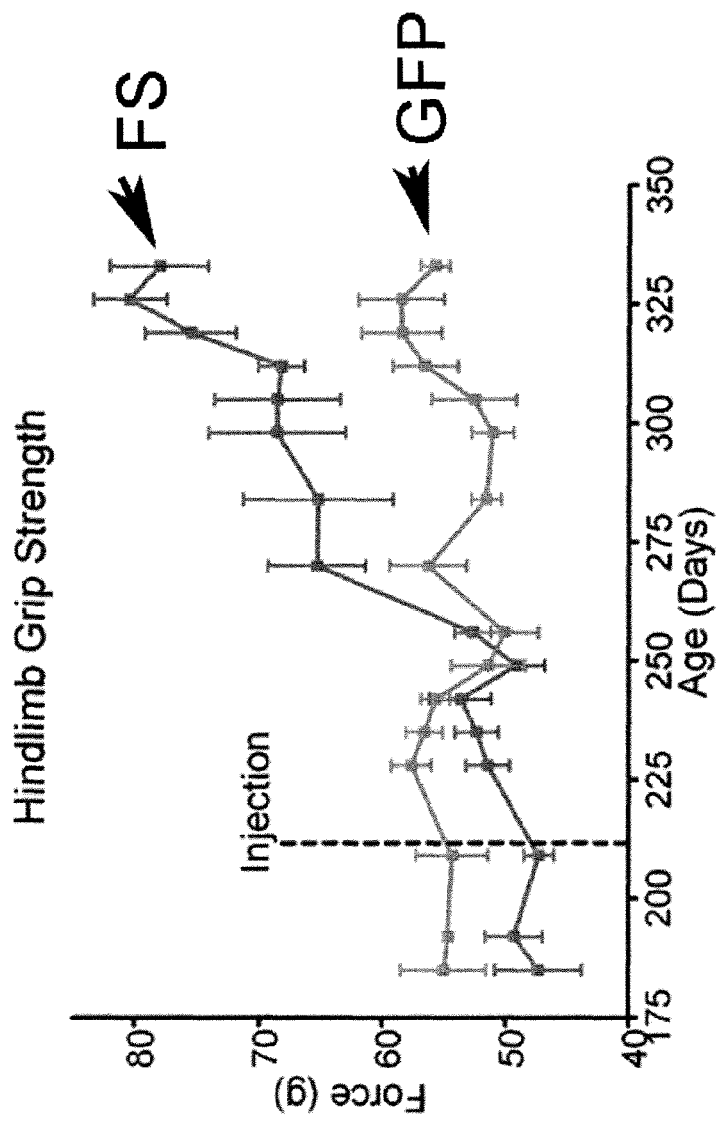
FIG. 19 demonstrates that a single injection of AAV1-FS can increase grip strength in aged mdx mice.

In experiments similar to those described in Example 3 and/or 4, at 210 days of age it was found that high dose ($1 \times 10^{11}$ AAV1 particles) FS administration increased muscle strength versus administration of AAV1-GFP in control animals ~60 days post administration (see FIG. 19). These results demonstrated that myostatin inhibition by FS treatment was beneficial in aged mdx animals that had undergone multiple rounds of muscle degeneration and regeneration.

Translation to a clinical parallel suggests that AAV-mediated FS gene therapy is indicated for the older DMD patient independent of replacing a missing gene and is indicated in combination therapy similar to that demonstrated for IGF-1 and mini-dystrophin gene replacement [Abmayr et al., Mol Ther., 12:441-450 (2005)].

Example 7

The effects of rAAV-follistatin-344 were studied in non-human primates using cynomologous macaques.

Figure 20:
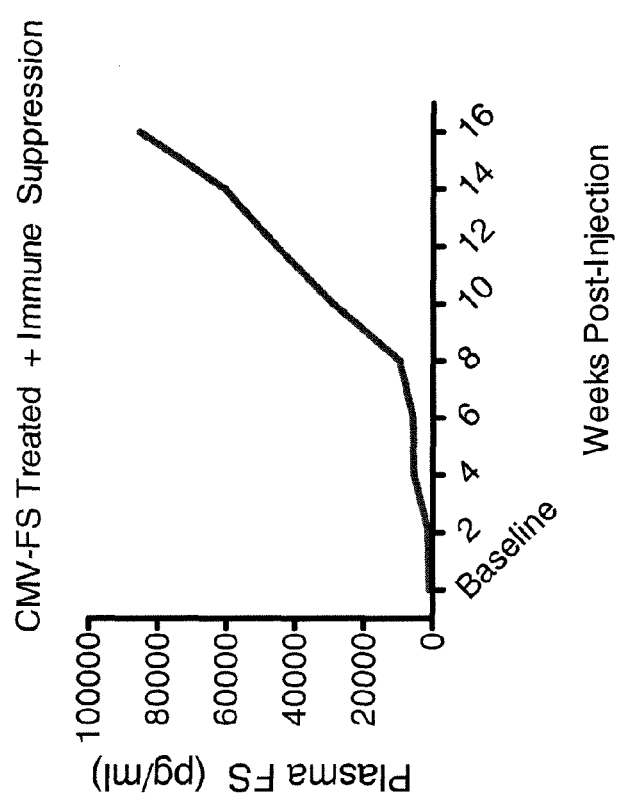
FIG. 20 depicts levels of FS in circulating plasma following AAV-CMV-FS administration to non-human primates.

The treatment included delivery of the follistatin sequences either under the control of the CMV promoter (rAAV-follistatin-344) or the mouse creatine kinase (MCK) promoter, to test the efficacy of a stronger (CMV) promoter versus a muscle specific promoter. The rAAV comprising the MCK promoter are designated "rAAV MCK follistatin-344" herein. Animals were injected into the quadriceps of one of their hindlimbs with $1 \times 10^{13}$ viral genomes in a total volume of 1.5 ml spread over three injections per quadriceps muscle in a volume of 0.5 ml per injection. Studies conducted to date have been accompanied by an immunosuppression regimen of Tacrolimus (1.5 mg/kg body weight) and microphenylate (50 mg/kg body weight) administered daily 1 week prior to vector delivery and daily post-vector injection. Animals have been followed bi-weekly for any evidence of toxicity, immune response and levels of Follistatin. No adverse events have been noted in any of the studies conducted to date, that includes a total of 6 animals (3 animals with CMV-, 3 animals with MCK-Follistatin). All animals have had detectable levels of Follistatin detected in the plasma, with the greatest amounts found in the CMV-Follistatin treated animals (FIG. 20).

Figure 21:
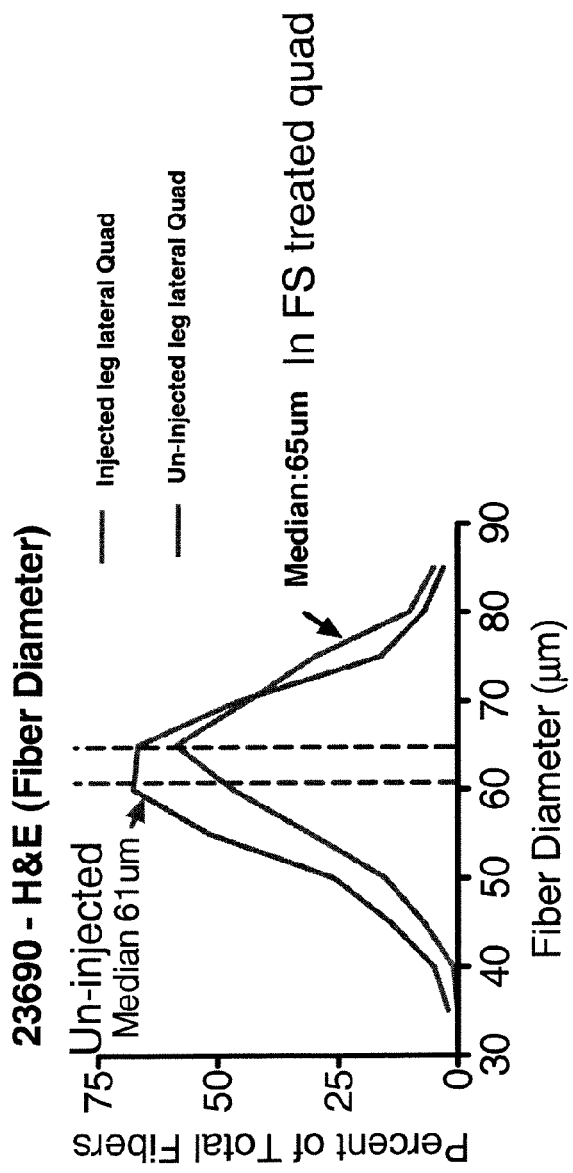
FIG. 21 depicts an analysis of fiber size showing muscle hypertrophy in MCK-FS injected quads compared to non-injected quads.

A biopsy of muscle from the rAAV MCK follistatin-344 treated animals demonstrated a significant increase in the diameter of myofibers in the injected muscles indicating that the lower expressed MCK-Follistatin was having biological effect to induce muscle hypertrophy in treated animals at 14-weeks post-injection (FIG. 21).

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

We claim:

1. A method of improving muscle function in an animal in need thereof comprising the step of administering to the animal by intramuscular injection a composition comprising one or more infectious encapsidated rAAVs, each rAAV comprising a rAAV genome comprising AAV inverted terminal repeats flanking a polynucleotide encoding follistatin-344, wherein the polynucleotide is operatively linked to transcriptional control DNA and wherein the genome lacks AAV rep and cap DNA.

* * * * *

UNITED STATES PATENT AND TRADEMARK OFFICE
CERTIFICATE OF CORRECTION

PATENT NO. : 8,895,309 B2
APPLICATION NO. : 12/516995
DATED : November 25, 2014
INVENTOR(S) : Brian K. Kaspar et al.

It is certified that error appears in the above-identified patent and that said Letters Patent is hereby corrected as shown below:

In the Specification

Before the claims, insert

```
--SEQUENCE LISTING

<110>  Nationwide Children's Hospital

<120>  Myostatin Inhibition for Enhancing Muscle Function and/or
       Improving Muscle Function

<130>  28335/42141

<140>  US 12/516,995
<141>  2010-03-22

<150>  US 60/861,602
<151>  2006-11-29

<160>  12

<170>  PatentIn version 3.4
```

Signed and Sealed this
Fifteenth Day of September, 2015

Michelle K. Lee
*Director of the United States Patent and Trademark Office*

<210> 1
<211> 1189
<212> DNA
<213> Homo sapiens

<220>
<223> Follistatin UCSD

<400> 1
| | | | | | |
|---|---|---|---|---|---|
| atggtccgcg | cgaggcacca | gccgggtggg | ctttgcctcc | tgctgctgct | gctctgccag | 60 |
| ttcatggagg | accgcagtgc | ccaggctggg | aactgctggc | tccgtcaagc | gaagaacggc | 120 |
| cgctgccagg | tcctgtacaa | gaccgaactg | agcaaggagg | agtgctgcag | caccggccgg | 180 |
| ctgagcacct | cgtggaccga | ggaggacgtg | aatgacaaca | cactcttcaa | gtggatgatt | 240 |
| ttcaacgggg | gcgcccccaa | ctgcatcccc | tgtaaagaaa | cgtgtgagaa | cgtggactgt | 300 |
| ggacctggga | aaaaatgccg | aatgaacaag | aagaacaaac | cccgctgcgt | ctgcgccccg | 360 |
| gattgttcca | acatcacctg | gaagggtcca | gtctgcgggc | tggatgggaa | aacctaccgc | 420 |
| aatgaatgtg | cactcctaaa | ggcaagatgt | aaagagcagc | cagaacaact | gaaagtccag | 480 |
| taccaaggca | gatgtaaaaa | gacttgtcgg | gatgtttttct | gtccaggcag | ctccacatgt | 540 |
| gtggtggacc | agaccaataa | tgcctactgt | gtgacctgta | atcggatttg | cccagagcct | 600 |
| gcttcctctg | agcaatatct | ctgtgggaat | gatggagtca | cctactccag | tgcctgccac | 660 |
| ctgagaaagg | ctacctgcct | gctgggcaga | tctattggat | tagcctatga | gggaaagtgt | 720 |
| atcaaagcaa | agtcctgtga | agatatccag | tgcactggtg | ggaaaaaatg | tttatgggat | 780 |
| ttcaaggttg | ggagaggccg | gtgttccctc | tgtgatgagc | tgtgccctga | cagtaagtcg | 840 |
| gatgagcctg | tctgtgccag | tgacaatgcc | acttatgcca | gcgagtgtgc | catgaaggaa | 900 |
| gctgcctgct | cctcaggtgt | gctactggaa | gtaaagcact | ccggatcttg | caactgaatc | 960 |
| tgcccgtaaa | acctgagcca | ttgattcttc | agaactttct | gcagtttttg | acttcataga | 1020 |
| ttatgcttta | aaaaattttt | tttaacttat | tgcataacag | cagatgccaa | aaacaaaaaa | 1080 |
| agcatctcac | tgcaagtcac | ataaaaatgc | aacgctgtaa | tatggctgta | tcagagggct | 1140 |

```
ttgaaaacat acactgagct gcttctgcgc tgttgttgtc cgtatttaa                    1189
```

```
<210>  2
<211>  391
<212>  PRT
<213>  Homo sapiens

<220>
<223>  Follistatin UCSD

<400>  2

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140
```

Leu Leu Lys Ala Arg Cys Lys Glu Gln Pro Glu Gln Leu Lys Val Gln
145                 150                 155                 160

Tyr Gln Gly Arg Cys Lys Lys Thr Cys Arg Asp Val Phe Cys Pro Gly
                165                 170                 175

Ser Ser Thr Cys Val Val Asp Gln Thr Asn Asn Ala Tyr Cys Val Thr
            180                 185                 190

Cys Asn Arg Ile Cys Pro Glu Pro Ala Ser Ser Glu Gln Tyr Leu Cys
            195                 200                 205

Gly Asn Asp Gly Val Thr Tyr Ser Ser Ala Cys His Leu Arg Lys Ala
            210                 215                 220

Thr Cys Leu Leu Gly Arg Ser Ile Gly Leu Ala Tyr Glu Gly Lys Cys
225                 230                 235                 240

Ile Lys Ala Lys Ser Cys Glu Asp Ile Gln Cys Thr Gly Gly Lys Lys
                245                 250                 255

Cys Leu Trp Asp Phe Lys Val Gly Arg Gly Arg Cys Ser Leu Cys Asp
            260                 265                 270

Glu Leu Cys Pro Asp Ser Lys Ser Asp Glu Pro Val Cys Ala Ser Asp
            275                 280                 285

Asn Ala Thr Tyr Ala Ser Glu Cys Ala Met Lys Glu Ala Ala Cys Ser
290                 295                 300

Ser Gly Val Leu Leu Glu Val Lys His Ser Gly Ser Cys Asn Ile Cys
305                 310                 315                 320

Pro Asn Leu Ser His Phe Phe Arg Thr Phe Cys Ser Phe Leu His Arg
                325                 330                 335

```
Leu Cys Phe Lys Lys Ile Phe Leu Thr Tyr Cys Ile Thr Ala Asp Ala
            340                 345                 350

Lys Asn Lys Lys Ser Ile Ser Leu Gln Val Thr Lys Cys Asn Ala Val
            355                 360                 365

Ile Trp Leu Tyr Gln Arg Ala Leu Lys Thr Tyr Thr Glu Leu Leu Leu
    370                 375                 380

Arg Cys Cys Cys Pro Tyr Leu
385                 390

<210>  3
<211>  1035
<212>  DNA
<213>  Homo sapiens

<220>
<223>  Follistatin 344 precursor

<400>  3
```

| | | | | | |
|---|---|---|---|---|---|
| atggtccgcg | cgaggcacca | gccgggtggg | ctttgcctcc | tgctgctgct | gctctgccag | 60 |
| ttcatggagg | accgcagtgc | ccaggctggg | aactgctggc | tccgtcaagc | gaagaacggc | 120 |
| cgctgccagg | tcctgtacaa | gaccgaactg | agcaaggagg | agtgctgcag | caccggccgg | 180 |
| ctgagcacct | cgtggaccga | ggaggacgtg | aatgacaaca | cactcttcaa | gtggatgatt | 240 |
| ttcaacgggg | gcgcccccaa | ctgcatcccc | tgtaaagaaa | cgtgtgagaa | cgtggactgt | 300 |
| ggacctggga | aaaaatgccg | aatgaacaag | aagaacaaac | cccgctgcgt | ctgcgccccg | 360 |
| gattgttcca | acatcacctg | gaagggtcca | gtctgcgggc | tggatggaaa | acctaccgc | 420 |
| aatgaatgtg | cactcctaaa | ggcaagatgt | aaagagcagc | cagaactgga | agtccagtac | 480 |
| caaggcagat | gtaaaaagac | ttgtcgggat | gttttctgtc | caggcagctc | cacatgtgtg | 540 |
| gtggaccaga | ccaataatgc | ctactgtgtg | acctgtaatc | ggatttgccc | agagcctgct | 600 |
| tcctctgagc | aatatctctg | tgggaatgat | ggagtcacct | actccagtgc | ctgccacctg | 660 |

```
agaaaggcta cctgcctgct gggcagatct attggattag cctatgaggg aaagtgtatc    720
aaagcaaagt cctgtgaaga tatccagtgc actggtggga aaaaatgttt atgggatttc    780
aaggttggga gaggccggtg ttccctctgt gatgagctgt gccctgacag taagtcggat    840
gagcctgtct gtgccagtga caatgccact tatgccagcg agtgtgccat gaaggaagct    900
gcctgctcct caggtgtgct actggaagta aagcactccg gatcttgcaa ctccatttcg    960
gaagacaccg aggaagagga ggaagatgaa gaccaggact acagctttcc tatatcttct   1020
attctagagt ggtaa                                                    1035
```

<210> 4
<211> 344
<212> PRT
<213> Homo sapiens

<220>
<223> Follistatin 344 precursor

<400> 4

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95
```

```
Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285
```

```
        Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn Ser Ile Ser
        305                 310                 315                 320

Glu Asp Thr Glu Glu Glu Glu Glu Asp Glu Asp Gln Asp Tyr Ser Phe
                        325                 330                 335

Pro Ile Ser Ser Ile Leu Glu Trp
                    340

<210>   5
        <211>   954
        <212>   DNA
        <213>   Homo sapiens

<220>
        <223>   Follistatin 317 precursor

<400>   5
        atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaaatgccg aatgaacaag aagaacaaac cccgctgcgt ctgcgccccg     360
gattgttcca acatcacctg gaagggtcca gtctgcgggc tggatgggaa aacctaccgc     420
aatgaatgtg cactcctaaa ggcaagatgt aaagagcagc cagaactgga agtccagtac     480
caaggcagat gtaaaaagac ttgtcgggat gttttctgtc caggcagctc cacatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
```

```
agaaaggcta cctgcctgct gggcagatct attggattag cctatgaggg aaagtgtatc    720
aaagcaaagt cctgtgaaga tatccagtgc actggtggga aaaaatgttt atgggatttc    780
aaggttggga gaggccggtg ttccctctgt gatgagctgt gccctgacag taagtcggat    840
gagcctgtct gtgccagtga caatgccact tatgccagcg agtgtgccat gaaggaagct    900
gcctgctcct caggtgtgct actggaagta aagcactccg gatcttgcaa ctga          954
```

<210> 6
<211> 317
<212> PRT
<213> Homo sapiens

<220>
<223> Follistatin 317 precursor

<400> 6

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110
```

```
Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
            165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
            245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300
```

```
Gly Val Leu Leu Glu Val Lys His Ser Gly Ser Cys Asn
305                 310                 315
```

```
<210>   7
<211>   792
<212>   DNA
<213>   Homo sapiens

<220>
<223>   FLRG

<400>   7
atgcgtcccg gggcgccagg gccactctgg cctctgccct gggggggccct ggcttgggcc      60 gtgggcttcg tgagctccat gggctcgggg aaccccgcgc ccggtggtgt ttgctggctc     120
cagcagggcc aggaggccac ctgcagcctg gtgctccaga ctgatgtcac ccgggccgag     180
tgctgtgcct ccggcaacat tgacaccgcc tggtccaacc tcacccaccc ggggaacaag     240
atcaacctcc tcggcttctt gggccttgtc cactgccttc cctgcaaaga ttcgtgcgac     300
ggcgtggagt gcggcccggg caaggcgtgc cgcatgctgg ggggccgccc gcgctgcgag     360
tgcgcgcccg actgctcggg gctcccggcg cggctgcagg tctgcggctc agacggcgcc     420
acctaccgcg acgagtgcga gctgcgcgcc gcgcgctgcc gcggccaccc ggacctgagc     480
gtcatgtacc ggggccgctg ccgcaagtcc tgtgagcacg tggtgtgccc gcggccacag     540
tcgtgcgtcg tggaccagac gggcagcgcc cactgcgtgg tgtgtcgagc ggcgccctgc     600
cctgtgccct ccagccccgg ccaggagctt gcggcaaca acaacgtcac ctacatctcc     660
tcgtgccaca tgcgccaggc cacctgcttc ctgggccgct ccatcggcgt gcgccacgcg     720
ggcagctgcg caggcacccc tgaggagccg ccaggtggtg agtctgcaga agaggaagag     780
aacttcgtgt ga                                                         792
```

```
<210>  8
<211>  263
<212>  PRT
<213>  Homo sapiens

<220>
<223>  FLRG

<400>  8
```

| | | | | | | | | | | | | | | |
|---|---|---|---|---|---|---|---|---|---|---|---|---|---|---|
| Met | Arg | Pro | Gly | Ala | Pro | Gly | Pro | Leu | Trp | Pro | Leu | Pro | Trp | Gly | Ala |
| 1 | | | | 5 | | | | | 10 | | | | | 15 | |

Leu Ala Trp Ala Val Gly Phe Val Ser Ser Met Gly Ser Gly Asn Pro
                20                  25                  30

Ala Pro Gly Gly Val Cys Trp Leu Gln Gln Gly Gln Glu Ala Thr Cys
            35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
        130                 135                 140

```
Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
            195                 200                 205

Glu Leu Cys Gly Asn Asn Asn Val Thr Tyr Ile Ser Ser Cys His Met
210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
            245                 250                 255

Glu Glu Glu Glu Asn Phe Val
                260

<210> 9
<211> 1716
<212> DNA
<213> Homo sapiens

<220>
<223> GASP-1

<400> 9
atgtgtgccc cagggtatca tcggttctgg tttcactggg ggctgctgtt gctgctgctc      60
ctcgaggctc cccttcgagg cctagcactg ccacccatcc gatactccca tgcgggcatc     120
tgccccaacg acatgaaccc caacctctgg gtggatgccc agagcacctg caagcgagag     180
```

```
tgtgaaacag accaggaatg tgagacctat gagaaatgct gccccaatgt gtgtgggacc    240
aagagctgtg tggcagcccg ctacatggat gtgaaaggga agaaggggcc tgtaggcatg    300
cccaaggagg ccacatgtga ccatttcatg tgcctgcagc agggctctga gtgtgacatc    360
tgggacggcc agcccgtgtg taagtgcaaa gatcgctgtg agaaggagcc cagcttcacc    420
tgtgcctctg atggccttac ctactacaac cgttgcttca tggacgccga agcctgctcc    480
aagggcatca cactgtctgt ggtcacctgt cgttatcact tcacctggcc taacaccagc    540
cctccaccgc ctgagaccac ggtgcatccc accaccgcct ctccggagac tctcgggctg    600
gacatggcag ccccagccct gctcaaccac cctgtccatc agtcagtcac cgtgggtgag    660
actgtgagtt tcctctgtga cgtggtaggc cggcctcggc cagagctcac ttgggagaaa    720
cagctggagg accgagagaa tgttgtcatg aggcccaacc acgtgcgtgg taatgtggtg    780
gtcactaaca ttgcccagct ggtcatctac aacgtccagc cccaggatgc tggcatatac    840
acctgtacag ctcgaaatgt cgctggtgtc ctgagggctg acttcccgtt gtcggtggtc    900
aggggtggtc aggccagggc cacttcagag agcagtctca atggcacagc ttttccagca    960
acagagtgcc tgaagccccc agacagtgag gactgtggag aggagcagac acgctggcac   1020
ttcgacgccc aggctaacaa ctgcctcact ttcacctttg ccactgcca ccacaatctc   1080 aaccactttg agacctacga ggcctgtatg ctggcttgta tgagtgggcc attggccacc   1140
tgcagcctgc ctgccctgca agggccttgc aaagcttatg tcccacgctg ggcctacaac   1200
agccagacag gcctatgcca gtccttcgtc tatggcggct gtgagggcaa cggtaacaac   1260
tttgaaagcc gtgaggcttg tgaggagtcg tgtcccttcc cgagggg taa ccagcactgc   1320 cgggcctgca agccccggca aaaacttgtt accagcttct gtcggagtga ctttgtcatc   1380
ctgggcaggg tctctgagct gaccgaggag caagactcgg ccgtgccct ggtgaccgtg   1440 gatgaggtct aaaagatga aagatgggc ctcaagtttc tgggccggga gcctctggaa   1500
gtcaccctgc ttcatgtaga ctggacctgt ccttgcccca acgtgacagt gggtgagaca   1560
ccactcatca tcatggggga ggtggacggc ggcatggcca tgctgagacc cgatagcttt   1620
```

```
gtgggggcat cgagcacacg gcgggtcagg aagctccgtg aggtcatgta caagaaaacc    1680
tgtgacgtcc tcaaggactt cctgggcttg caatga                              1716

<210>  10
<211>  571
<212>  PRT
<213>  Homo sapiens

<220>
<223>  GASP-1

<400>  10
```

Met Cys Ala Pro Gly Tyr His Arg Phe Trp Phe His Trp Gly Leu Leu
1               5                  10                  15

Leu Leu Leu Leu Leu Glu Ala Pro Leu Arg Gly Leu Ala Leu Pro Pro
                20                  25                  30

Ile Arg Tyr Ser His Ala Gly Ile Cys Pro Asn Asp Met Asn Pro Asn
            35                  40                  45

Leu Trp Val Asp Ala Gln Ser Thr Cys Lys Arg Glu Cys Glu Thr Asp
    50                  55                  60

Gln Glu Cys Glu Thr Tyr Glu Lys Cys Cys Pro Asn Val Cys Gly Thr
65                  70                  75                  80

Lys Ser Cys Val Ala Ala Arg Tyr Met Asp Val Lys Gly Lys Lys Gly
                85                  90                  95

Pro Val Gly Met Pro Lys Glu Ala Thr Cys Asp His Phe Met Cys Leu
            100                 105                 110

Gln Gln Gly Ser Glu Cys Asp Ile Trp Asp Gly Gln Pro Val Cys Lys
        115                 120                 125

```
Cys Lys Asp Arg Cys Glu Lys Glu Pro Ser Phe Thr Cys Ala Ser Asp
    130                 135                 140

Gly Leu Thr Tyr Tyr Asn Arg Cys Phe Met Asp Ala Glu Ala Cys Ser
145             150                 155                     160

Lys Gly Ile Thr Leu Ser Val Val Thr Cys Arg Tyr His Phe Thr Trp
                165                 170                 175

Pro Asn Thr Ser Pro Pro Pro Glu Thr Thr Val His Pro Thr Thr
            180             185                 190

Ala Ser Pro Glu Thr Leu Gly Leu Asp Met Ala Ala Pro Ala Leu Leu
        195                 200                 205

Asn His Pro Val His Gln Ser Val Thr Val Gly Glu Thr Val Ser Phe
    210                 215                 220

Leu Cys Asp Val Val Gly Arg Pro Arg Pro Glu Leu Thr Trp Glu Lys
225                 230                 235                 240

Gln Leu Glu Asp Arg Glu Asn Val Val Met Arg Pro Asn His Val Arg
                245                 250                 255

Gly Asn Val Val Val Thr Asn Ile Ala Gln Leu Val Ile Tyr Asn Val
                260                 265                 270

Gln Pro Gln Asp Ala Gly Ile Tyr Thr Cys Thr Ala Arg Asn Val Ala
        275                 280                 285

Gly Val Leu Arg Ala Asp Phe Pro Leu Ser Val Val Arg Gly Gly Gln
        290                 295                 300

Ala Arg Ala Thr Ser Glu Ser Ser Leu Asn Gly Thr Ala Phe Pro Ala
305                 310                 315                 320
```

```
Thr Glu Cys Leu Lys Pro Pro Asp Ser Glu Asp Cys Gly Glu Gln
                325             330             335

Thr Arg Trp His Phe Asp Ala Gln Ala Asn Asn Cys Leu Thr Phe Thr
            340             345             350

Phe Gly His Cys His His Asn Leu Asn His Phe Glu Thr Tyr Glu Ala
            355             360             365

Cys Met Leu Ala Cys Met Ser Gly Pro Leu Ala Thr Cys Ser Leu Pro
    370             375             380

Ala Leu Gln Gly Pro Cys Lys Ala Tyr Val Pro Arg Trp Ala Tyr Asn
385             390             395                         400

Ser Gln Thr Gly Leu Cys Gln Ser Phe Val Tyr Gly Gly Cys Glu Gly
                405             410             415

Asn Gly Asn Asn Phe Glu Ser Arg Glu Ala Cys Glu Glu Ser Cys Pro
            420             425             430

Phe Pro Arg Gly Asn Gln His Cys Arg Ala Cys Lys Pro Arg Gln Lys
        435             440             445

Leu Val Thr Ser Phe Cys Arg Ser Asp Phe Val Ile Leu Gly Arg Val
        450             455             460

Ser Glu Leu Thr Glu Glu Gln Asp Ser Gly Arg Ala Leu Val Thr Val
465             470             475                         480

Asp Glu Val Leu Lys Asp Glu Lys Met Gly Leu Lys Phe Leu Gly Arg
            485             490             495

Glu Pro Leu Glu Val Thr Leu Leu His Val Asp Trp Thr Cys Pro Cys
            500             505             510
```

```
        Pro Asn Val Thr Val Gly Glu Thr Pro Leu Ile Ile Met Gly Glu Val
                515                 520                 525

Asp Gly Gly Met Ala Met Leu Arg Pro Asp Ser Phe Val Gly Ala Ser
            530                 535                 540

Ser Thr Arg Arg Val Arg Lys Leu Arg Glu Val Met Tyr Lys Lys Thr
        545                 550                 555                 560

Cys Asp Val Leu Lys Asp Phe Leu Gly Leu Gln
                        565                 570

<210>  11
<211>  1035
<212>  DNA
<213>  Homo sapiens

<220>
<223>  Follistatin 344

<400>  11
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaatgccg aatgaacaag aagaacaaac cccgctgcgt ctgcgccccg     360
gattgttcca acatcacctg gaagggtcca gtctgcgggc tggatgggaa acctaccgc     420 aatgaatgtg cactcctaaa ggcaagatgt aaagagcagc agaactgga agtccagtac     480 caaggcagat gtaaaaagac ttgtcgggat gttttctgtc caggcagctc cacatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
```

```
agaaaggcta cctgcctgct gggcagatct attggattag cctatgaggg aaagtgtatc    720
aaagcaaagt cctgtgaaga tatccagtgc actggtggga aaaaatgttt atgggatttc    780
aaggttggga gaggccggtg ttccctctgt gatgagctgt gccctgacag taagtcggat    840
gagcctgtct gtgccagtga caatgccact tatgccagcg agtgtgccat gaaggaagct    900
gcctgctcct caggtgtgct actggaagta aagcactccg gatcttgcaa ctccatttcg    960
gaagacaccg aggaagagga ggaagatgaa gaccaggact acagctttcc tatatcttct   1020
attctagagt ggtaa                                                    1035
```

<210> 12
<211> 344
<212> PRT
<213> Homo sapiens

<220>
<223> Follistatin 344

<400> 12

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95
```

```
Asn Val Asp Cys Gly Pro Gly Lys Lys Cys Arg Met Asn Lys Lys Asn
        100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
        130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
        210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285
```

```
Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp --
        340
```

UNITED STATES PATENT AND TRADEMARK OFFICE
CERTIFICATE OF CORRECTION

| | |
|---|---|
| PATENT NO. | : 8,895,309 B2 |
| APPLICATION NO. | : 12/516995 |
| DATED | : November 25, 2014 |
| INVENTOR(S) | : Brian K. Kaspar et al. |

It is certified that error appears in the above-identified patent and that said Letters Patent is hereby corrected as shown below:

In the Specification

At Column 1, Lines 5-8, the following government support clause should be deleted:
"This invention was developed with partial government support under grant number NS052530 from the National Institutes of Health and Project A.L.S. The government may have certain rights in this invention."

Signed and Sealed this
Twenty-fourth Day of May, 2022

*Katherine Kelly Vidal*

Katherine Kelly Vidal
*Director of the United States Patent and Trademark Office*